US006436640B1

(12) United States Patent
Simmons et al.

(10) Patent No.: US 6,436,640 B1
(45) Date of Patent: Aug. 20, 2002

(54) USE OF LNA IN MASS SPECTROMETRY

(75) Inventors: Adrian Simmons, Amersham; Clifford Smith, Tring, both of (GB)

(73) Assignee: Exiqon A/S, Vedback (DK)

( * ) Notice: Subject to any disclaimer, the term of this patent is extended or adjusted under 35 U.S.C. 154(b) by 0 days.

(21) Appl. No.: 09/528,705

(22) Filed: Mar. 18, 2000

Related U.S. Application Data

(60) Provisional application No. 60/127,357, filed on Apr. 1, 1999.

(30) Foreign Application Priority Data

Mar. 18, 1999 (DK) .......................... 1999 00381

(51) Int. Cl.$^7$ ............................ C12Q 1/68; C12P 19/34
(52) U.S. Cl. .......................... 435/6; 435/91.1; 435/91.2
(58) Field of Search ........................... 435/6, 91.1, 91.2

(56) References Cited

U.S. PATENT DOCUMENTS

| | | | | |
|---|---|---|---|---|
| 5,547,835 A | * | 8/1996 | Koster | 435/6 |
| 5,605,798 A | * | 2/1997 | Koster | 435/6 |
| 6,043,031 A | * | 3/2000 | Koster et al. | 435/6 |
| 6,197,498 B1 | * | 3/2001 | Koster | 435/5 |
| 6,221,601 B1 | * | 4/2001 | Koster et al. | 435/6 |
| 6,221,605 B1 | * | 4/2001 | Koster | 435/6 |
| 6,235,478 B1 | * | 5/2001 | Koster | 435/6 |
| 6,258,538 B1 | * | 7/2001 | Koster et al. | 435/6 |
| 6,268,144 B1 | * | 7/2001 | Koster | 435/6 |
| 6,268,490 B1 | * | 7/2001 | Imanishi et al. | 536/23.1 |
| 6,277,573 B1 | * | 8/2001 | Koster | 435/6 |
| 6,300,076 B1 | * | 10/2001 | Koster | 435/6 |
| 6,303,315 B1 | * | 10/2001 | Skouv | 435/6 |
| 6,316,198 B1 | * | 11/2001 | Skouv et al. | 435/6 |

FOREIGN PATENT DOCUMENTS

| | | |
|---|---|---|
| EP | 0 305 929 B1 | 3/1989 |
| WO | WO 94/16101 | 7/1994 |
| WO | WO 94/21822 | 9/1994 |
| WO | WO 95/15001 | 6/1995 |
| WO | WO 96/29431 | 9/1996 |
| WO | WO 98/12734 | 3/1998 |

OTHER PUBLICATIONS

S. Obika et al., *Tetrahedron Letters*, 39:5401–5404 (1998).
P. Nielsen et al., *J. Chem. Soc. Perkin Trans.*, 1:3423–3433 (1997).
A. Koshkin et al., *Tetrahedron*, 54:3607–3630 (1998).
R. Kumar et al., *Bioorganic & Medicinal Chemistry Letters*, 8:2219–2222 (1998).
R. Lewis, *BioPhotonics International*, 53–55 (1998).
A. Marshall et al., *Nature Biotechnology*, 16:27–31 (1998).
S. Laken et al., *Nature Biotechnology*, 16:1352–1356 (1998).
A. Persidis, *Nature Biotechnology*, 16:981–983 (1998).
F. Sanger et al., *Proc. Natl. Acad. Sci. USA*, 74(12):5463–5467 (1977).
M. Innis et al., *Proc. Natl. Acad. Sci. USA*, 85:9436–9440 (1988).

* cited by examiner

*Primary Examiner*—Kenneth R. Horlick
(74) *Attorney, Agent, or Firm*—Peter F. Corless; Dianne M. Rees; Edwards & Angell, LLP

(57) ABSTRACT

DNA and RNA diagnostics based on mass spectrometry, e.g. Matrix-Assisted Laser Desorption/Ionisation Time-of-Flight (MALDI-TOF) mass spectrometry, Electrospray (ES) mass spectrometry, Ion Cyclotron Resonance (ICR) mass spectrometry, Fourier Transform mass spectrometry, or combinations thereof, where fully or partially LNA modified DNA probes are used in order to enhance stability and resolution. The invention in particular relates to a process for detecting a target nucleic acid sequence of a nucleic acid molecule or for detecting a mutation in a nucleic acid sequence of a nucleic acid molecule, wherein (a) the nucleic acid molecule or (b) a part of the nucleic acid molecule or (c) an oligonucleotide complementary to the sequence or at least a sub-sequence of the nucleic acid molecule is analysed by mass spectrometry in order to obtain direct or indirect information about the target nucleic acid sequence or mutation, and wherein the process involves the hybridisation of an LNA modified oligonucleotide to the nucleic acid molecule.

17 Claims, No Drawings

USE OF LNA IN MASS SPECTROMETRY

This application claims the benefit of U.S. Provisional Application(s) No(s).: Application No(s).: 60/127,357 filling date Apr, 01, 1999.

FIELD OF THE INVENTION

The present invention relates to DNA diagnostics based on mass spectrometry where fully or partially LNA modified DNA probes are used in order to enhance stability and resolution.

BACKGROUND OF THE INVENTION

The genetic information of all living organisms (e.g. animals, plants and micro-organisms) is encoded in deoxyribonucleic acid (DNA). In humans, the complete genome is comprised of about 100,000 genes located on 24 chromosomes (The Human Genome, T. Strachan, BIOS Scientific Publishers, 1992). Each gene codes for a specific protein which after its expression via transcription and translation, fulfils a specific biochemical function within a living cell. Changes in a DNA sequence are known as mutations and can result in proteins with altered or in some cases even lost biochemical activities; this in turn can cause genetic disease. Mutations include nucleotide deletions, insertions or alterations (i.e. point mutations). Point mutations can be either "mis-sense", resulting in a change in the amino acid sequence of a protein or "nonsense" coding for a stop codon and thereby leading to a truncated protein. Furthermore, the detection of polymorphisms might be equally interesting.

More than 3000 genetic diseases are currently known (Human Genome Mutations, D. N. Cooper and M. Krawczak, BIOS Publishers, 1993), including hemophilias, thalassemias, Duchenne Muscular Dystrophy (DMD), Huntington's Disease (HD), Alzheimer's Disease and Cystic Fibrosis (CF). In addition to mutated genes, which result in genetic disease, certain birth defects are the result of chromosomal abnormalities such as Trisomy 21 (Down's Syndrome). Trisomy 13 (Patau Syndrome), Trisomy 18 (Edward's Syndrome), Monosomy X (Turner's Syndrome) and other sex chromosome aneuploidies such as Klienfelter's Syndrome (XXY). Further, there is growing evidence that certain DNA sequences may predispose an individual to any of a number of diseases such as diabetes, arteriosclerosis, obesity, various autoimmune diseases and cancer (e.g. colorectal, breast, ovarian, lung). Viruses, bacteria, fungi and other infectious organisms contain distinct nucleic acid sequences, which are different from the sequences contained in the host cell. Therefore, infectious organisms can also be detected and identified based on their specific DNA sequences.

Since the sequence of about 16 nucleotides is specific on statistical grounds even for the size of the human genome, relatively short nucleic acid sequences can be used to detect normal and defective genes in higher organisms and to detect infectious microorganisms (e.g. bacteria, fungi, protists and yeast) and viruses. DNA sequences can serve as a fingerprint for detection of different individuals within the same species.

Analysis of nucleic acid molecules by mass spectrometry has thus met increasing interest in recent years.

In general, mass spectrometry provides a means of "weighing" individual molecules by ionising the molecules in vacuo and making them "fly" by volatilisation. Under the influence of combinations of electric and magnetic fields, the ions follow trajectories depending on their individual mass (m) and charge (z). In the range of molecules with low molecular weight, mass spectrometry has long been part of the routine physical-organic repertoire for analysis and characterisation of organic molecules by the determination of the mass of the parent molecular ion. In addition, by arranging collisions of this parent molecular ion with other particles (e.g. argon atoms), the molecular ion is fragmented forming secondary ions by the so-called collision induced dissociation (CID). The fragmentation pattern/pathway very often allows the derivation of detailed structural information. Many applications of mass spectrometric methods are known in the art, particularly in biosciences, and can be found summarised in *Methods in Enzymology*, Vol. 193:"Mass Spectrometry" (J. A. McCloskey, editor), 1990, Academic Press, New York and "Mass spectrometry for Biotechnology" by G. Siuzdak, 1996, Academic Press.

Two more recent ionisation/desorption techniques are electrospray/ionspray (ES) and matrix-assisted laser desorption/ionisation (MALDI). ES mass spectrometry has been introduced by Fenn et al. (*J. Phys. Chem.* 88, 4451–59 (1984); PCT Application No. WO 90/14148) and current applications are summarised in recent review articles (R. D. Smith et al., Anal. Chem., 62, .882–89 (1990) and B. Ardrey. Electrospray Mass Spectrometry, *Spectroscopy Europe*, 4, 10–18 (1992)). As a mass analyser, a quadrupole is most frequently used. The determination of molecular weights in femtomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyser. The MALDI-TOF mass spectrometry has been introduced by Hillenkamp et al. ("Matrix Assisted UV-Laser Desorption/Ionisation: A New Approach to Mass Spectrometry of Large Biomolecules." *Biological Mass Spectrometry* (Burlingame and McCloskey, editors), Elsevier Science Publishers, Amsterdam, pp. 49–60, 1990). Since, in most cases, no multiple molecular ion peaks are produced with this technique, the mass spectra, in principle, look simpler compared to ES mass spectrometry.

WO 94/16101 (Koster) describes DNA sequencing by means of mass spectrometry and WO 94/21822 (Koster) describes DNA sequencing by means of mass spectrometry via exonuclease degradation.

WO 96129431 (Sequenom) describes various ways of determining the sequence of and mutations in nucleic acid molecules by means of mass spectrometry analysis. It is described that introduction of mass differentiating markers facilitates the resolution of the mass spectrometry signals and thereby allows for multiplexing.

Bicyclic nucleotide analogues, i.e. nucleotide analogues containing bicyclic sugars, have been described in the literature. Substitution of natural nucleotides in oligonucleotides with bicyclic analogues has, however, often been performed at the cost of specificity or affinity.

Recently, however, Locked Nucleoside Analogues (LNA) have been described by Wengel and co-workers and others (see e.g. Nielsen et al., J. Chem. Soc. Perkin Trans. 1, 1997, p 3423; Koshkin et al., Tetrahedron 54 (1998), p 3607–3630; Kumar et al., Bioorg. Med. Chem. Lett. 8 (1998) 2219–2222; and Obika et al., Tetrahedron Lett. 39 (1998), 5401–5404), and it has been described that novel bicyclic nucleotide analogues exhibit improved affinity and specificity characteristics when incorporated into oligonucleotides. It is believed that a whole class of such modified nucleotide analogues possess the characteristics described by Wengel and co-workers.

SUMMARY OF THE INVENTION

The present applicants have found that the use of LNA modified oligonucleotides in processes for the detection of a target nucleic acid sequence of a nucleic acid molecule or for the detection of a mutation in a nucleic acid sequence of a nucleic acid molecule by mass spectrometry offers at least three major advantages, namely (a) the possibility of adjusting (typically increasing) the specificity and/or affinity of an oligonucleotide involved in the detection process for the nucleic acid molecule, (b) the direct inclusion of mass differentiation markers, and (c) increased stability of the LNA modified oligonucleotides under conditions of mass spectrometry.

Thus, the present invention provides a process for detecting a target nucleic acid sequence of a nucleic acid molecule or for detecting a mutation in a nucleic acid sequence of a nucleic acid molecule, wherein (a) the nucleic acid molecule or (b) a part of the nucleic acid molecule or (c) an oligonucleotide complementary to the sequence or at least a sub-sequence of the nucleic acid molecule is analysed by mass spectrometry in order to obtain direct or indirect information about said target nucleic acid sequence or mutation, and wherein the process involves the hybridisation of an LNA modified oligonucleotide to the nucleic acid molecule.

The present invention, thus, provides a highly useful and valuable improvement to the known diagnostic method for analysis of DNA.

DETAILED DESCRIPTION OF THE INVENTION

As described above, the present invention provides a process for detecting a target nucleic acid sequence of a nucleic acid molecule or for detecting a mutation in a nucleic acid sequence of a nucleic acid molecule, wherein (a) the nucleic acid molecule or (b) a part of the nucleic acid molecule or (c) an oligonucleotide complementary to the sequence or at least a sub-sequence of the nucleic acid molecule is analysed by mass spectrometry in order to obtain direct or indirect information about said target nucleic acid sequence or mutation, and wherein the process involves the hybridisation of an LNA modified oligonucleotide to the nucleic acid molecule.

Such processes (however not utilising the advantageous LNA modified oligonucleotides) are described in WO 96/29431, WO 94/16101 and WO 94/21822 which are hereby incorporated by reference.

As the hybridisation between the LNA modified oligonucleotide and the nucleic acid molecule plays an important role in the process according to the invention, it is often desirable to modify the hybridisation properties so that either the specificity or the affinity, or both, are adjusted so as to obtain more reliable results. With the present invention, it is now possible to improve the specificity and/or the affinity and at the same time include mass differentiation markers which can be used for improving the resolution of the mass spectrum. Furthermore, it is desirable that the stability of an oligonucleotide to be analysed by mass spectrometry is improved so as to provide more reliable and reproducible results.

As will be apparent from the following, the LNA modified oligonucleotide which is hybridised to the nucleic acid molecule is typically selected from detector oligonucleotides, capture oligonucleotides, primers, extended primers, ligation educts and ligation products, of course depending on the construction and type of the detection analysis.

In a preferred variant which fully exploits the advantageous features of LNA modified oligonucleotides (specificity/affinity and mass differentiation), the LNA modified oligonucleotide is analysed by mass spectrometry in order to obtain information about the target nucleic acid sequence or mutation. It should, however, be understood that improved affinity and specificity alone may also be highly useful, e.g. for capture of nucleic acid molecules which then are analysed directly by mass spectrometry (see below).

Although LNA modified oligonucleotides are highly useful as capture probes in mass spectrometry, it should be understood that in order to exploit all the advantages of using LNA modified oligonucleotides in mass spectrometry, the LNA modified oligonucleotide is preferably the oligomer to be analysed by mass spectroscopy. Thus, the LNA modified oligonucleotide which is hybridised to the nucleic acid molecule is preferably the oligonucleotide which is analysed by mass spectroscopy in order to obtain direct or indirect information about the sequence or mutation of said target nucleic acid. Thus, the LNA modified oligonucleotide is preferably selected from detector oligonucleotides, primers, extended primers, ligation educts and ligation products in the mass spectrometry process.

To facilitate mass spectrometric analysis, a nucleic acid molecule containing a nucleic acid sequence to be detected can be immobilised to a solid support. Examples of appropriate solid supports include beads (e.g. silica gel, controlled pore glass, magnetic, Sephadex, Sepharose, cellulose), flat surfaces or chips (e.g. glass fibre filters, glass surfaces, metal surfaces (steel, gold, silver, aluminium, copper and silicon), capillaries, plastic (e.g. polyethylene, polypropylene, polyamide, polyvinylidenedifluoride membranes or microtiter plates)), or pins or combs made from similar materials comprising beads or flat surfaces or beads placed into pits in flat surfaces such as wafers (e.g. silicon wafers).

Immobilisation can be accomplished, for example, based on hybridisation between a capture oligonucleotide, which has already been immobilised to the support and a complementary nucleic acid sequence, which is also contained within the nucleic acid molecule containing the nucleic acid sequence to be detected. So that hybridisation between the complementary nucleic acid molecules is not hindered by the support, the capture nucleic acid can include a spacer region of at least about five nucleotides in length between the solid support and the capture nucleic acid sequence. The duplex formed will be cleaved under the influence of the laser pulse and desorption can be initiated. The solid support-bound capture oligonucleotide can be presented through natural oligoribo- or oligodeoxyribonucleotide as well as analogues (e.g. thio-modified phosphodiester or phosphotriester backbone) or employing oligonucleotide mimetics such as PNA analogues which render the base sequence less susceptible to enzymatic degradation and hence increases overall stability of the solid support-bound capture base sequence.

Within the present invention, the capture oligonucleotide is preferably an immobilised LNA modified oligonucleotide.

Alternatively, a target detection site can be directly linked to a solid support via a reversible or irreversible bond between an appropriate functionality (L') on the target nucleic acid molecule (T) and an appropriate functionality (L) on a capture molecule bound to the solid support. A reversible linkage can be such that it is cleaved under the conditions of mass spectrometry (i.e. a photocleavable bond such as a charge transfer complex or a labile bond being formed between relatively stable organic radicals). Furthermore, the linkage can be formed with L' being a quaternary ammonium group, in which case, preferably, the surface of the solid support carries negative charges which repel the negatively charged nucleic acid backbone and thus facilitate the desorption required for analysis by a mass spectrometer.

Desorption can occur either by the heat created by the laser pulse and/or, depending on L' by specific absorption of laser energy which is in resonance with the L' chromophore.

By way of example, the L–L' chemistry can be of a type of disulfide bond (chemically cleavable, for example, by mercaptoethanol or dithioerythrol), a biotin/streptavidin system, a heterobifunctional derivative of a trityl ether group which can be cleaved under mildly acidic conditions as well as under conditions of mass spectrometry, a levulinyl group cleavable under almost neutral conditions with a hydrazinium/acetate buffer, an arginine—arginine or lysine—lysine bond cleavable by an endopeptidase enzyme like trypsin or a pyrophosphate bond cleavable by a pyrophosphatase, or a ribonucleotide bond in between the oligodeoxynucleotide sequence, which can be cleaved, for example, by a ribonuclease or alkali.

The functionalities, L and L', can also form a charge transfer complex and thereby form the temporary L–L' linkage. Since in many cases the "charge-transfer band" can be determined by UV/vis spectrometry, the laser energy can be tuned to the corresponding energy of the charge-transfer wavelength and thus, a specific desorption off the solid support can be initiated. Those skilled in the art will recognise that several combinations can serve this purpose and that the donor functionality can be either on the solid support or coupled to the nucleic acid molecule to be detected or vice versa.

In yet another approach, a reversible L–L' linkage can be generated by homolytically forming relatively stable radicals. Under the influence of the laser pulse, desorption (as discussed above) as well as ionisation will take place at the radical position.

Those skilled in the art will recognise that other organic radicals can be selected and that, in relation to the dissociation energies needed to homolytically cleave the bond between them. a corresponding laser wavelength can be selected (see e.g. Reactive Molecules by C. Wentrup, John Wiley B: Sons, 1984).

An anchoring function L' can also be incorporated into a target capturing sequence (TCS) by using appropriate primers during an amplification procedure, such as PCR, LCR or transcription amplification.

The capture oligonucleotide or the target nucleic acid can also be immobilised directly to the solid support by means of a photochemical coupling agent, e.g. an anthra quinone reagent as described in WO 96/31577 (Havsteen Jakobsen and Koch).

In general, the instant invention provides mass spectrometric processes for detecting a particular nucleic acid sequence of nucleic acid molecules. Such nucleic acid molecules are often obtained from biological samples. As used herein, the term "biological sample" refers to any material obtained from any living source (e.g. human, animal, plant, bacteria, fungi, protist virus). For use in the invention, the biological sample should contain a nucleic acid molecule. Examples of appropriate biological samples for use in the instant invention include: solid materials (e.g. tissue, cell pellets, biopsies) and biological fluids (e.g. urine, blood, saliva, amniotic fluid, mouth wash).

Nucleic acid molecules can be isolated from a particular biological sample using any of a number of procedures, which are well-known in the art, the particular isolation procedure chosen being appropriate for the particular biological sample. For example, freeze/thaw and alkaline lysis procedures can be useful for obtaining nucleic acid molecules from solid materials, heat and alkaline lysis procedures can be useful for obtaining nucleic acid molecules from urine, and proteinase K extraction can be used to obtain nucleic acid from blood.

To obtain an appropriate quantity of a nucleic acid molecules on which to perform mass spectrometry, amplification may be necessary. Examples of appropriate amplification procedures for use in the invention include: cloning (Sambrook et al., Molecular Cloning : A Laboratory Manual. Cold Spring Harbor Laboratory Press. 1989). polymerase chain reaction (PCR) (C. R. Newton and A. Graham. PCR, BIOS Publishers, 1994), ligase chain reaction (LCR) (Wiedmann, M., et. al., (1994) *PCR Methods Appl.*, Vol. 3Pp. 57–64; F. Barany, *Proc. Natl. Acad. Sci USA* 88, 189–93 (1991), strand displacement amplification (SDA) (G. Terrance Walker et al., *Nucleic Acids Res* 22, 2670–77 (1994)) and variations such as RT-PCR (Higuchi. et al., *Biol/Technology* 11, 1026–1030 (1993)), allele-specific amplification (ASA) and transcription based processes.

Nucleic acids molecules include deoxyribonucleic acids (DNA) and ribonucleic acids (RNA).

The mass spectrometry analysis typically utilises matrix-Assisted Laser Desorption/Ionisation Time-of-Flight (MALDI-TOF) mass spectrometry, Electrospray (ES) mass spectrometry, Ion Cyclotron Resonance (ICR) mass spectrometry, Fourier Transform mass spectrometry, or combinations thereof. These techniques are well-known to the person skilled in the art.

Preferred mass spectrometer formats for use in the invention are matrix assisted laser desorption ionisation (MALDI), electrospray (ES), ion cyclotron resonance (ICR) and Fourier Transform. For ES, the samples, dissolved in water or in a volatile buffer, are injected either continuously or discontinuously into an atmospheric pressure ionisation interface (API) and then mass analysed by a quadrupole. The generation of multiple ion peaks which can be obtained using ES mass spectrometry can increase the accuracy of the mass determination. Even more detailed information on the specific structure can be obtained using an MS/MS quadrupole configuration. TOF can also be used with ES for increased accuracy and resolution. In MALDI mass spectrometry, various mass analysers can be used e.g., magnetic sector/magnetic deflection instruments in single or triple quadrupole mode (MS/MS). Fourier transform and time-of-flight (TOF) configurations as is known in the art of mass spectrometry. For the desorption/ionisation process, numerous matrix/laser combinations can be used. Ion-trap and reflectron configurations can also be employed.

Although, the use of LNA modified oligomers is believed to improve the stability of oligomers to be analysed by mass spectrometry (see below), it might be in certain instances be advantageous to (further) "condition" nucleic acid molecules, for example to decrease the laser energy required for volatilisation and/or to (further) minimise fragmentation. Conditioning is preferably performed while a target detection site is immobilised. An example of conditioning is modification of the phosphodiester backbone of the nucleic acid molecule (e.g. cation exchange), which can be useful for eliminating peak broadening due to a heterogeneity in the cations bound per nucleotide unit. Contacting a nucleic acid molecule with an alkylating agent such as alkyliodide iodoacetamide, β-iodoethanol, or 2,3-epoxy-1-propanol, the monothio phosphodiester bonds of a nucleic acid molecule can be transformed into a phosphotriester bond. Likewise, phosphodiester bonds may be transformed to uncharged derivatives employing trialkylsilyl chlorides. Further conditioning involves incorporating nucleotides which reduce sensitivity for depurination (fragmentation during mass spectrometry) such as N7- or N9-deazapurine nucleotides, or RNA building blocks or using oligonucleotide triesters or incorporating phosphorothioate functions which are alkylated or employing oligonucleotide mimetics such as PNA. Conditioning may also be relevant when LNA modified oligonucleotides are used, even though the LNAs in the LNA modified oligonucleotides may be constructed so that conditioning is unnecessary, e.g. by utilising LNA modified oligonucleotides where the phosphate backbone is modified (see below).

For certain applications, it may be useful to simultaneously detect more than one (mutated) loci on a particular captured nucleic acid fragment (on one spot of an array) or it may be useful to perform parallel processing by using oligonucleotide or oligonucleotide mimetic arrays on various solid supports. "Multiplexing" can be achieved by several different methodologies. For example, several mutations can be simultaneously detected on one target sequence by employing corresponding detector oligonucleotides. However, the molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities M1–M3 into the detector oligonucleotide. Here, LNA modification of the detector oligonucleotide can provide the necessary molecular weight differences in that a bridge of incorporated LNAs in themselves provide at least a increase in molecular weight by 10 D per modification (one carbon substituting two hydrogens in the case of a —O—CH$_2$- bridge substituting a —H and an —OH substituent, e.g. as in the case where R$^{2*}$ and R$^{4*}$ together forms a —O—CH$_2$- bridge in an LNA, see below). Similarly, the introduction of a —S—CH$_2$— or —NR—CH$_2$— bridge will offer to possibility of introducing other combination of mass differences. Thus, introduction of further mass-modifying functionalities are generally not necessary.

Mass modifying moieties can if desired be attached, for instance, to either the 5'-end of the oligonucleotide-, to the nucleobase (or bases), to the phosphate backbone, and to the 2-position of the nucleoside (nucleosides) or/and to the terminal 3'-position. Examples of mass modifying moieties include, for example, a halogen, an azido, or of the type, XR, wherein X is a linking group and R is a mass-modifying functionality. The mass-modifying functionality can thus be used to introduce further defined mass increments into the oligonucleotide molecule.

Here the mass-modifying moiety, M, can be attached either to the nucleobase (in case of the C$^7$-deazanucleosides also to C-7), to the triphosphate group at the alpha phosphate, or to the 3'-position of the sugar ring of the nucleoside triphosphate. Furthermore, the mass-modifying functionality can be added so as to affect chain termination, such as by attaching it to the 3'-position of the sugar ring in the nucleoside triphosphate. For those skilled in the art, it is clear that many combinations can serve the purpose of the invention equally well. In the same way, those skilled in the art will recognise that chain-elongating nucleoside triphosphates can also be mass-modified in a similar fashion with numerous variations and combinations in functionality and attachment positions. Alternatively, mass modifications can be introduced by incorporating stable isotopes, e.g. $^{32}$S, $^{33}$S, $^{34}$S, $^{36}$S.

Without limiting the scope of the invention, the mass-modification, M, can be introduced for X in XR as well as using oligo-/polyethylene glycol derivatives for R. The mass-modifying increment in this case is 44, i.e. five different mass-modified species can be generated by just changing m from 0 to 4 thus adding mass units of 45 (m=0), 89 (m=1), 133 (m=2), 177 (m=3) and 221 (m=4) to the nucleic acid molecule. The oligo/polyethylene glycols can also be monoalkylated by a lower alkyl such as methyl, ethyl, propyl, isopropyl, t-butyl and the like. A selection of linking functionalities, X, are also illustrated. Other chemistries can be used in the mass-modified compounds, as for example, those described recently in *Oligonucleotides and Analogues. A Practical Approach*, F. Eckstein, editor, IRL Press, Oxford, 1991.

In yet another embodiment, various mass-modifying functionalities, R, other than oligo/polyethylene glycols, can be selected and attached via appropriate linking chemistries, X. A simple mass-modification can be achieved by substituting H for halogens like F, Cl, Br and/or I, or pseudohalogens such as SCN, NCS, or by using different alkyl, aryl or aralkyl moieties such as methyl, ethyl, propyl, isopropyl, t-butyl, hexyl, phenyl, substituted phenyl, benzyl, or functional groups such as CH$_2$F, CHF$_2$, CF$_3$, Si(CH$_3$)$_3$, Si(CH$_3$)$_2$ (C$_2$H$_5$), Si(CH$_3$)(C$_2$H$_5$)$_2$, Si(C$_2$H$_5$)$_3$. Yet another mass-modification can be obtained by attaching homo- or heteropeptides through the nucleic acid molecule (e.g. detector (D)) or nucleoside triphosphates. One example useful in generating mass-modified species with a mass increment of 57 is the attachment of oligoglycines, e.g., mass modifications of 74 (r=1, m=0), 131 (t=1, m=2), 188 (r=1, m=3), 245 (r=1, m=4) are achieved. Simple oligoamides also can be used, e.g., mass-modifications of 74 (r=1, m=0), 88 (r=2, m=0), 102 (r=3, m=0), 116 (r=4, m=0), etc. are obtainable. For those skilled in the art, it will be obvious that there are numerous possibilities in addition to those mentioned above.

Different mass-modified detector oligonucleotides can be used to simultaneously detect all possible variants/mutants simultaneously. Alternatively, all four base permutations at the site of a mutation can be detected by designing and positioning a detector oligonucleotide, so that it serves as a primer for a DNA/RNA polymerase. For example, mass modifications also can be incorporated during the amplification process.

It should be understood that the above-mentioned mass modifications primarily apply to any native nucleotides in the oligonucleotides or LNA modified oligonucleotides since the described mass modifications already are integral features of the LNA modified oligonucleotides (see the definitions below).

In a further preferred embodiment, the sample is conditioned by mass differentiating at least two detector oligonucleotides or oligonucleotide mimetics to detect and distinguish at least two target nucleic acid sequences simultaneously, where at least one detector oligonucleotide is a LNA modified oligonucleotide. This application is especially relevant in connection with multiplexing.

In an embodiment of the process of the present invention, the target nucleic acid sequence is a DNA fingerprint or is implicated in a disease or condition selected from the group consisting of a genetic disease, a chromosomal abnormality, a genetic predisposition, a viral infection, a fungal infection, a bacterial infection and a protist infection. This is particularly interesting since there is growing evidence that certain DNA sequences may predispose an individual to any of a number of diseases such as diabetes arteriosclerosis, obesity, various autoimmune diseases and cancer (e.g. colorectal, breast, ovarian, lung); chromosomal abnormality (either prenatally or postnatally); or a predisposition to a disease or condition (e.g. obesity, arteriosclerosis, cancer). Also, the detection of "DNA fingerprints". e.g. polymorphisms, such as "microsatellite sequences", are useful for determining identity or heredity (e.g. paternity or maternity).

Depending on the biological sample, the diagnosis for a genetic disease, chromosomal pneuploidy or genetic predisposition can be preformed either pre- or postnatally.

Viruses, bacteria, fungi and other infectious organisms contain distinct nucleic acid sequences, which are different from the sequences contained in the host cell. Detecting or quantitating nucleic acid sequences that are specific to the infectious organism is important for diagnosing or monitoring infection.

One process for detecting a wildtype ($D^{wt}$) and/or a mutant ($D^{mut}$) sequence in a target (T) nucleic acid molecule is as follows: A specific capture sequence (C; which might be the LNA modified oligonucleotide) is attached to a solid support (ss) via a spacer (S). In addition, the capture sequence is chosen to specifically interact with a complementary sequence on the target sequence (T), the target capture site (TCS) to be detected through hybridisation. However, if the target detection site (TDS) includes a mutation, X, which increases or decreases the molecular weight, mutated TDS can be distinguished from wildtype by mass spectrometry. For example, in the case of an adenine base (dA) insertion, the difference in molecular weights between $D^{wt}$ and $D^{mut}$ would be about 314 daltons.

Preferably, the detector nucleic acid (D; which might be the LNA modified oligonucleotide) is designed such that the mutation would be in the middle of the molecule and the flanking regions are short enough so that a stable hybrid would not be formed if the wildtype detector oligonucleotide ($D^{wt}$) is contacted with the mutated target detector sequence as a control. The mutation can also be detected if the mutated detector oligonucleotide ($D^{mut}$) with the matching base at the mutated position is used for hybridisation. If a nucleic acid obtained from a biological sample is heterozygous for the particular sequence (i. e. contain both $D^{wt}$ and $D^{mut}$), both $D^{wt}$ and Dmut will be bound to the appropriate strand and the mass difference allows both $D_{wt}$ and $D_{mut}$ to be detected simultaneously.

The process of this invention makes use of the known sequence information of the target sequence and known mutation sites. Although new mutations can also be detected. For example transcription of a nucleic acid molecule obtained from a biological sample can be specifically digested using one or more nucleases and the byfragments captured on a solid support carrying the corresponding complementary nucleic acid sequences. Detection of hybridisation and the molecular weights of the captured target sequences provide information on whether and where in a gene a mutation is present. Alternatively, DNA can be cleaved by one or more specific endonucleases to form a mixture of fragments. Comparison of the molecular weights between wildtype and mutant fragment mixtures results in mutation detection.

The process of the present invention can be performed in a number of ways depending on the nature of the nucleic acid and the type of result desired. Some of the possible variants are described in the following.

One variant for detecting a target nucleic acid sequence present in a biological sample, comprising the steps of:
a) obtaining a nucleic acid molecule from a biological sample;
b) immobilising the nucleic acid molecule onto a solid support to produce an immobilised nucleic acid molecule;
c) hybridising a detector oligonucleotide with the immobilised nucleic acid molecule and removing unhybridised detector oligonucleotide:
d) ionising and volatilising the product of step c); and
e) detecting the detector oligonucleotide by mass spectrometry, wherein detection of the detector oligonucleotide indicates the presence of the target nucleic acid sequence in the biological sample.

In this variant, a LNA modified oligonucleotide can either be the detector oligonucleotide or be used to immobilise the nucleic acid molecule.

This variant is especially relevant where the successful hybridisation of a detector oligonucleotide is a positive marker for a specific sequence or a specific mutation in the nucleic acid sequence. It is of course preferred that the detector oligonucleotide is an LNA modified oligonucleotide.

The nucleic acid molecule is typically obtained from a biological sample. This nucleic acid molecule may be purified and amplified before analysis as described above. Preferably, the target nucleic acid sequence is amplified prior to step b), e.g. by an amplification procedure selected from the group consisting of: cloning, transcription based amplification, the polymerase chain reaction (PCR), the ligase chain reaction (LCR), and strand displacement amplification (SDA).

The immobilisation, step b), is can be accomplished either by direct bonding of the nucleic acid molecule to a solid support (e.g. via a linker) by means of a photochemical coupling reagent (e.g. an anthraquinone) or by means of a biotin/streptavidin system. Alternatively, the immobilisation may be accomplished by hybridisation between a complementary capture nucleic acid molecule, which has been previously immobilised to a solid support, and a complementary specific sequence on the target nucleic acid sequence. Such a complementary capture nucleic acid molecule is preferably an LNA modified oligonucleotide.

In an interesting alternative, immobilisation is accomplished by hybridisation between an array of complementary capture nucleic acid molecules, which have been previously immobilised to a solid support, and a portion of the nucleic acid molecule, which is distinct from the target nucleic acid sequence. The complementary capture nucleic acid molecules are typically oligonucleotides or oligonucleotide mimetics, preferably LNA modified oligonucleotides.

A detector nucleic acid molecule (e.g. an oligonucleotide or oligonucleotide mimetic), which is complementary to the target detection site can then be contacted with the target detection site and formation of a duplex indicating the presence of the target detection site can be detected by mass spectrometry. In preferred embodiments, the target detection site is amplified prior to detection and the nucleic acid molecules are conditioned. In a further preferred embodiment, the target detection sequences are arranged in a format that allows multiple simultaneous detections (multiplexing), as well as parallel processing using oligonucleotide arrays ("DNA chips"—see e.g. Nature Biotechnology, Vol. 16, October 1998, page 981–983).

It is furthermore preferred that the immobilisation in step b) is reversible so that the nucleic acid molecule can be liberated either for purification or for analytical purposes.

One intriguing feature of the present invention, which is applicable for the variants where a detector oligonucleotide is analysed, is the possibility of designing an array of oligonucleotides wherein the sequence (or a subsequence) is a direct function of the molecular weight. If, e.g., C→G mutations are found in three positions (A,B,C) of a nucleic acid molecule, seven possible mutations (2*2*2-1) beside the wild-type exist. By construction of eight "unmodified" detector oligonucleotides, it is not possible to distinguish between a single mutation i position A, B and C. However, by, e.g., constructing eight LNA modified detector oligonucleotides where the three oligonucleotides corresponding to a single mutation in A, B or C have different numbers of LNAs incorporated, and where the three oligonucleotides corresponding to double mutations in AB, BC or AC also have different numbers of LNAs incorporated, each and every oligonucleotide will have a distinctive mass. Thus, by addition of the mixture of oligonucleotides, only one LNA modified oligonucleotide will hybridise, and by subsequent mass spectroscopic analysis, the number and location of the mutations is directly detectable.

It is believed that the principle is equally applicable for detection of an unknown shorter sequence in a nucleic acid molecule. By addition of a mixture of, e.g., 64 (4*4*4) LNA modified oligonucleotides with distinctive molecular weights, it is possible to "scan" three unknown positions in a nucleic acid by hybridisation and obtain direct information by subsequent mass spectrometry analysis. Based on the excellent specificity and affinity characteristics of certain LNAs, this is considered realistic.

Another variant, for detecting a target nucleic acid sequence present in a biological sample, comprising the steps of:
a) obtaining a nucleic acid molecule containing a target nucleic acid sequence from a biological sample:
b) amplifying the target nucleic acid sequence using an appropriate amplification procedure thereby obtaining an amplified target nucleic acid sequence;
c) hybridising a detector oligonucleotide with the nucleic acid molecule and removing unhybridised detector oligonucleotide;
d) ionising and volatilising the product of step c); and
e) detecting the detector oligonucleotide by mass spectrometry, wherein detection of the detector oligonucleotide indicates the presence of the target nucleic acid sequence in the biological sample.

In this variant it equivalent to the above variant, however, immobilisation is not a mandatory step. As above, it is preferred that the detector oligonucleotide is an LNA modified oligonucleotide. Also as above, the target nucleic acid is preferably amplified by an amplification procedure selected from the group consisting of: cloning, transcription based amplification, the polymerase chain reaction (PCR), the ligase chain reaction (LCR), and strand displacement amplification (SDA). Also, the amplified target nucleic acid sequences are preferably immobilised onto a solid support to produce immobilised target nucleic acid sequences, and hybridisation between a complementary capture nucleic acid molecule (preferably an LNA modified oligonucleotide), which has been previously immobilised to a solid support, and the target nucleic acid sequence is subsequently conducted.

It is furthermore preferred that the immobilisation in step b) is reversible so that the nucleic acid molecule can be liberated either for purification or for analytical purposes.

A further variant for detecting a target nucleic acid sequence present in a biological sample, comprising the steps of:
a) obtaining a target nucleic acid sequence from a biological sample:
b) replicating the target nucleic acid sequence, thereby producing a replicated nucleic acid molecule;
c) specifically digesting the replicated nucleic acid molecule using at least one appropriate nuclease, thereby producing digested fragments:
d) immobilising the digested fragments onto a solid support containing complementary capture nucleic acid sequences to produce immobilised fragments; and
e) analysing the immobilised fragments by mass spectrometry, wherein hybridisation and the determination of the molecular weights of the immobilised fragments provide information on the target nucleic acid sequence.

In this variant, LNA modified oligonucleotides may be used as capture nucleic acids or LNA monomers may be used in the replication of the nucleic acid molecule.

In this variant, nucleic acid molecules which have been replicated from a nucleic acid molecule obtained from a biological sample can be specifically digested using one or more nucleases (using deoxyribonucleases for DNA or ribonucleases for RNA) and the fragments captured on a solid support carrying the corresponding complementary sequences. Hybridisation events and the actual molecular weights of the captured target sequences provide information on whether and where mutations in the gene are present. The array can be analysed spot by spot using mass spectrometry. DNA can be similarly digested using a cocktail of nucleases including restriction endonucleases. In a preferred embodiment, the nucleic acid fragments are conditioned prior to mass spectrometric detection.

After step a), the target nucleic acid sequence may be replicated into DNA using mass modified deoxynucleoside and/or dideoxynucleoside triphosphates and RNA dependent DNA polymerase. The mass modified deoxyribonucleoside and/or dideoxynucleoside triphosphates may be monomeric LNAs.

Alternatively, the target nucleic acid sequence is replicated into RNA using mass modified ribonucleoside and/or 3'-deoxynucleoside triphosphates and DNA dependent RNA polymerase. The mass modified ribonucleoside and/or 3'-deoxynucleoside triphosphates may be monomeric LNAs.

As a further alternative, the target nucleic acid may be replicated into DNA using mass modified deoxynucleoside and/or dideoxynucleoside triphosphates and a DNA dependent DNA polymerase. Also here, the mass modified deoxyribonucleoside and/or dideoxynucleoside triphosphates may be monomeric LNAs.

The complementary capture nucleic acid sequences are typically oligonucleotides or oligonucleotide mimetics, such as LNA modified oligonucleotides. The immobilisation is preferable reversible.

A still further variant for detecting a target nucleic acid sequence present in a biological sample, comprising the steps of:

a) obtaining a nucleic acid molecule containing a target nucleic acid sequence from a biological sample;

b) contacting the target nucleic acid sequence with at least one primer, said primer having 3' terminal base complementarity to the target nucleic acid sequence;

c) contacting the product of step b) with an appropriate polymerase enzyme and sequentially with one of the four nucleoside triphosphates;

d) ionising and volatilising the product of step c); and e) detecting the product of step d) by mass spectrometry, wherein the molecular weight of the product indicates the presence or absence of a mutation next to the 3'-end of the primer in the target nucleic acid sequence.

In this variant at least one primer with 3' terminal base complementarity to an allele (mutant or normal) is hybridised with a target nucleic acid molecule, which contains the allele. An appropriate polymerase and a complete set of nucleoside triphosphates or only one of the nucleoside triphosphates are used in separate reactions to furnish a distinct extension of the primer. Only if the primer is appropriately annealed (i. e. no 3' mismatch) and if the correct (i. e. complementary) nucleotide is added, will the primer be extended. Products can be resolved by molecular weight shifts as determined by mass spectrometry.

In this variant, the primer is an LNA modified oligonucleotide.

A still further variant for detecting a target nucleotide present in a biological sample, comprising the steps of:

a) obtaining a nucleic acid molecule that contains a target nucleotide;

b) immobilising the nucleic acid molecule onto a solid support, to produce an immobilised nucleic acid molecule;

c) hybridising the immobilised nucleic acid molecule with a primer oligonucleotide that is complementary to the nucleic acid molecule at a site immediately 5' of the target nucleotide;

d) contacting the product of step c) with a complete set of dideoxynucleosides or 3'-deoxynucleoside triphosphates and a DNA dependent DNA polymerase, so that only the deoxynucleoside or 3'-deoxynucleoside triphosphate that is complementary to the target nucleotide is extended onto the primer;

e) ionising and volatilising the product of step d); and f) detecting the extended primer by mass spectrometry, to determine the identity of the target nucleotide.

In this variant, a nucleic acid molecule containing the nucleic acid sequence to be detected (i.e. the target) is initially immobilised to a solid support. Immobilisation can be accomplished, for example, based on hybridisation between a portion of the target nucleic acid molecule, which is distinct from the target detection site and a capture nucleic acid molecule, which has been previously immobilised to a solid support. Alternatively, immobilisation can be accomplished by direct bonding of the target nucleic acid molecule and the solid support. Preferably, there is a spacer (e.g. a nucleic acid molecule) between the target nucleic acid molecule and the support. A nucleic acid molecule that is complementary to a portion of the target detection site that is immediately 5' of the site of a mutation is then hybridised with the target nucleic acid molecule. The addition of a complete set of dideoxynucleosides or 3'-deoxynucleoside triphosphates (e.g. pppAdd, pppTdd, pppCdd and pppGdd) and a DNA dependent DNA polymerase allows for the addition only of the one dideoxynucleoside or 3'-deoxynucleoside triphosphate that is complementary to X. The hybridisation product can then be detected by mass spectrometry.

In this variant, either the a capture nucleic acid molecule or the extended primer is an LNA modified oligonucleotide. This latter is preferably the case and can either be accomplished by using an LNA modified oligonucleotide as primer or using LNAs monomers as substrates for the nucleic acid polymerase.

A still further variant for detecting a mutation in a nucleic acid molecule, comprising the steps of:

a) obtaining a nucleic acid molecule;

b) hybridising the nucleic acid molecule with an oligonucleotide probe, thereby forming a mismatch at the site of a mutation;

c) contacting the product of step b) with a single strand specific endonuclease;

d) ionising and volatilising the product of step c); and e) detecting the products obtained by mass spectrometry, wherein the presence of more than one fragment, indicates that the nucleic acid molecule contains a mutation.

Here, a target nucleic acid is hybridised with a complementary oligonucleotides that hybridise to the target within a region that includes a mutation M. The heteroduplex is then contacted with an agent that can specifically cleave at an unhybridised portion (e.g. a single strand specific endonuclease), so that a mismatch, indicating the presence of a mutation, results in the cleavage of the target nucleic acid. The two cleavage products can then be detected by mass spectrometry. Preferably, the oligonucleotide probe is an LNA modified oligonucleotide.

A even still further variant for detecting a target nucleic acid sequence present in a biological sample, comprising the steps of a) obtaining a nucleic acid containing a target nucleic acid sequence from a biological sample;

b) performing at least one hybridisation of the target nucleic acid sequence with a set of ligation educts and a thermostable DNA ligase, thereby forming a ligation product;

c) ionising and volatilising the product of step b); and d) detecting the ligation product by mass spectrometry and comparing the value obtained with a known value to determine the target nucleic acid sequence.

This variant is based on the ligase chain reaction (LCR) where a target nucleic acid is hybridised with a set of ligation educts and a thermostable DNA ligase, so that the ligase educts become covalently linked to each other, forming a ligation product. The ligation product can then be detected by mass spectrometry and compared to a known value. If the reaction is performed in a cyclic manner, the ligation product obtained can be amplified to better facilitate detection of small volumes of the target nucleic acid. Selection between wildtype and mutated primers at the ligation point can result in the detection of a point mutation. It is preferred that one of the ligation educts and/or the ligation product is an LNA modified oligonucleotide.

The processes of the invention provide for increased accuracy and reliability of nucleic acid detection by mass spectrometry. In addition, the processes allow for rigorous controls to prevent false negative or positive results. The processes of the invention avoid electrophoretic steps: labelling and subsequent detection of a label. In fact it is estimated that the entire procedure, including nucleic acid isolation, amplification, and mass spectrometry analysis requires only about 2–3 hours time. Therefore the instant disclosed processes of the invention are faster and less expensive to perform than existing DNA detection systems. In addition, because the instant disclosed processes allow the nucleic acid fragments to be identified and detected at the same time by their specific molecular weights (an unambiguous physical standard), the disclosed processes are also much more accurate and reliable than currently, available procedures. By using LNA modified oligonucleotides, it is, furthermore, possible to obtain improved stability of the oligonucleotide to be analysed by mass spectrometry.

In view of the above, it is preferred that the LNA modified oligonucleotide has a ubstantially similar or a higher affinity towards the nucleic acid sequence compared to a corresponding unmodified oligonucleotide. Thus, preferably, the LNA modified ligonucleotide (oligomer) comprises at least one nucleoside analogue which imparts to the oligomer a $T_m$ with a complementary DNA oligonucleotide which is at least 0.5° C. higher, such as at least 1.5° C. higher or 2.5° C. higher, preferably at least 3.5° C. higher, in particular at least 4.0° C. higher, especially at least 5.0° C. higher, than that of the corresponding unmodified reference oligonucleotide which does not comprise any nucleoside analogue. In particular, the $T_m$ of the oligomer is at least 2.5×N° C. higher, preferably at least 3.5×N° C. higher, in particular at least 4.0×N° C. higher, especially at least 5.0×N° C. higher, than that of the corresponding unmodified reference oligonucleotide which does not comprise any LNAs, where N is the number of LNAs.

Also preferably, in the case of hybridisation with a complementary RNA oligonucleotide, the at least one nucleoside analogue imparts to the oligomer a $T_m$ with the complementary DNA oligonucleotide which is at least 0.5° C. higher, such as at least 1.5° C. higher or 2.5 ° C. higher, 4.0° C. higher, preferably at least 5.0° C. higher, in particular at least 6.0° C. higher, especially at least 7.0° C. higher, than that of the corresponding unmodified reference oligonucleotide which does not comprise any nucleoside analogue. In particular, the $T_m$ of the oligomer is at least 4.0×N° C. higher, preferably at least 5.0×N° C. higher, in particular at least 6.0×N° C. higher, especially at least 7.0×N° C. higher, than that of the corresponding unmodified reference oligonucleotide which does not comprise any LNA nucleoside analogues, where N is the number of nucleoside analogues.

The term "corresponding unmodified reference oligonucleotide" is intended to mean an oligonucleotide solely consisting of naturally occurring nucleotides which represents the same nucleobases in the same absolute order (and the same orientation).

For the purpose of the above determination, the $T_m$ is measured under one of the following conditions:
a) 10 mM $Na_2HPO_4$, pH 7.0, 100 mM NaCl, 0.1 mM EDTA;
b) 10 mM $Na_2HPO_4$ pH 7.0, 0.1 mM EDTA; or
c) 3M tetrametylammoniumchlorid (TMAC), 10 mM $Na_2HPO_4$, pH 7.0, 0.1 mM EDTA; preferably under conditions a), at equimolar amounts (typically 1.0 μM) of the oligomer and the complementary DNA oligonucleotide.

The LNA modified oligonucleotide should also have a substantially similar or a higher specificity towards the nucleic acid sequence compared to a corresponding unmodified oligonucleotide. Thus, with respect to specificity and affinity, the oligomer, when hybridised with a partially complementary DNA oligonucleotide, or a partially complementary RNA oligonucleotide, having one or more mismatches with said oligomer, should exhibit a reduction in $T_m$, as a result of said mismatches, which is equal to or greater than the reduction which would be observed with the corresponding unmodified reference oligonucleotide which does not comprise any nucleoside analogues. Also, the oligomer should have substantially the same sensitivity of $T_m$ to the ionic strength of the hybridisation buffer as that of the corresponding unmodified reference oligonucleotide.

LNA Modified Oligomers and LNAs

The specific feature of the processes of the present invention is the use of LNA modified oligonucleotides in mass spectrometry detection of a target nucleic acid sequence of a nucleic acid molecule or in mass spectrometry detection of a mutation in a nucleic acid sequence of a nucleic acid molecule. As will be apparent from this disclosure as a whole, the possibility of varying the specificity and affinity between the nucleic acid molecule to be detected and the LNA modified oligonucleotide offers a number of possibilities for improvement of known techniques.

Thus, the present invention relates to processes which utilise oligomers (LNA modified oligonucleotides) comprising at least one nucleoside analogue (hereinafter termed "LNA") of the general formula I

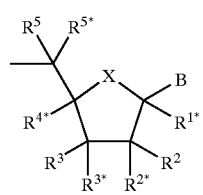

wherein X is selected from —O—, —S—, —N($R^{N*}$)—, —C($R^6R^{6*}$)—, —O—C($R^7R^{7*}$)—, —C($R^6R^{6*}$)—O—, —S—C($R^7R^{7*}$)—, —C($R^6R^{6*}$)—S—, —N($R^{N*}$)—C($R^7R^{7*}$)—, —C($R^6R^{6*}$)—N($R^{N*}$)—, and —C($R^6R^{6*}$)—C($R^7R^{7*}$)—, B is selected from hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$;

one of the substituents $R^2$, $R^{2*}$, $R^3$, and $R^{3*}$ is a group P*which designates an internucleoside linkage to a preceding monomer, or a 3'-terminal group;

one or two pairs of non-geminal substituents selected from the present substituents of $R^{1*}$, $R^{4*}$, $R^5$, $R^{5*}$, $R^6$, $R^{6*}$, $R^7$, $R^{7*}$, $R^{N*}$, and the ones of $R^2$, $R^{2*}$, $R^3$, and $R^{3*}$ not designating P* each designates a biradical consisting of 1–8 groups/atoms selected from —C($R^aR^b$)—, —C($R^a$)=C($R^a$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents $R^a$ and $R^b$ together may designate optionally substituted methylene (=$CH_2$), and wherein two non-geminal or geminal substitutents selected from $R^a$, $R^b$, and any of the substituents $R^{1*}$, $R^2$, $R^{2*}$, $R^3$, $R^{3*}$, $R^{4*}$, $R^5$, $R^{5*}$, $R^6$ and $R^{6*}$, $R^7$, and $R^{7*}$ which are present and not involved in P, P* or the biradical(s) together may form an associated biradical selected from biradicals of the same kind as defined before;

said pair(s) of non-geminal substituents thereby forming a mono- or bicyclic entity together with (i) the atoms to which said non-geminal substituents are bound and (ii) any intervening atoms; and each of the substituents $R^{1*}$, $R^2$, $R^{2*}$, $R^3$, $R^{4*}$, present and not involved in P, P* or the biradical(s), is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(NR$^N$)—where R$^N$ is selected from hydrogen and $C_{1-4}$-alkyl, and where two adjacent (non-geminal) substituents may designate an additional bond resulting in a double bond; and R$^{N*}$, when present and not involved in a biradical, is selected from hydrogen and $C_{1-4}$-alkyl;

and basic salts and acid addition salts thereof, and analogues enriched with stables isotopes.

The present invention furthermore utilises nucleoside analogues (hereinafter LNAs) of the general formula II

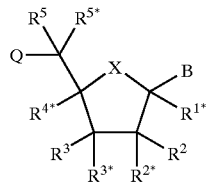

II wherein the substituent B is selected from nucleobases, DNA intercalators, photochemically active groups, thermochemically active groups, chelating groups, reporter groups, and ligands;

X is selected from —O—, —S—, —N(R$^{N*}$)—, and —C(R$^6$R$^{6*}$)—;

one of the substituents $R^2$, $R^{2*}$, $R^3$, and $R^{3*}$ is a group Q*;

each of Q and Q* is independently selected from hydrogen, azido, halogen, cyano, nitro, hydroxy, Prot-O—, Act-O—, mercapto, Prot-S—, Act-S—, $C_{1-6}$-alkylthio, amino, Prot-N(R$^H$)—, Act-N(R$^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-12}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, Act-O—$CH_2$—, aminomethyl, Prot-N(R$^H$)—$CH_2$—, Act-N(R$^H$)—$CH_2$—, carboxymethyl, sulphonomethyl, where Prot is a protection group for —OH, —SH, and —NH(R$^H$), respectively, Act is an activation group for —OH, —SH, and —NH(R$^H$), respectively, and R$^H$ is selected from hydrogen and $C_{1-6}$-alkyl;

(i) $R^{2*}$ and R4* together designate a biradical selected from —O—, —(CR*R*)$_{r+s*1}$—, —(CR*R*)$_r$—O—(CR$^{30}$ R*)$_s$—, —(CR*R*)$_r$—S—(CR*R*)$_s$—, —(CR*R*)$_r$—N(R*)—(CR*R*)$_s$—, —O—(CR*R*)$_{r+s}$—O—, —S—(CR*R*)$_{r+s}$—O—, —O—(CR*R*)$_{r+s}$—S—, —N(R*)—(CR*R*)$_{r+s}$—O—, —O—(CR*R*)$_{r+s}$—N(R*)—, —S—(CR*R*)$_{r+s}$—S—, —N(R*)—(CR*R*)$_{r+s}$—N(R*)—, —N(R*)—(CR*R*)$_{r+s}$—S—, and —S—(CR*R*)$_{r+s}$—N(R*)—;

(ii) $R^2$ and $R^3$ together designate a biradical selected from —O—, —(CR*R*)$_{r+s}$—, —(CR*R*)$_r$—O—(CR*R*)$_s$—, —(CR*R*)$_r$—S—(CR*R*)$_s$—, and —(CR*R*)$_r$—N(R*)—(CR*R*)$_s$—;

(iii) $R^{2*}$ and $R^3$ together designate a biradical selected from —O—, —(CR*R*)$_{r+s}$—, —(CR*R*)$_r$—O—(CR*R*)$_s$—, —(CR*R*)$_r$—S—(CR*R*)$_s$—, and —(CR*R*)$_r$—N(R*)—(CR*R*)$_s$—;

(iv) $R^3$ and $R^{4*}$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—;

(v) $R^3$ and $R^5$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—; or (vi) $R^{1*}$ and $R^{4*}$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—;

(vii) $R^{1*}$ and $R^{2*}$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—;

wherein each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R may together designate a double bond, and each of r and s is 0–3 with the proviso that the sum r*s is 1–4;

each of the substituents $R^{1*}$, $R^2$, $R^{2*}$, $R^3$, $R^{4*}$, $R^5$, and $R^{5*}$, which are not involved in Q, Q* or the biradical, is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl) amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(NR$^N$)— where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl;

and basic salts and acid addition salts thereof, and analogues enriched with stable isotopes.

When used herein, the term "LNA" (<u>L</u>ocked <u>N</u>ucleoside <u>A</u>nalogues) refers to bi- and tri-cyclic nucleoside analogues as defined herein, either incorporated in the oligomer (LNA modified oligonucleotides) (general formula I) or as discrete chemical species (general formula II). The term "monomeric LNA" specifically refers to the latter case.

As mentioned above, oligomers (LNA modified oligonucleotides) comprising one or more bi-, tri-, or polycyclic nucleoside analogues (hereinafter termed "LNA"). It has been found that the incorporation of such LNAs in place of, or as a supplement to, e.g., known nucleosides confer interesting and highly useful properties to an oligonucleotide. Bicyclic LNAs and oligonucleotides incorporating such LNAs seem especially interesting within the scope of the present invention.

Each of the possible LNAs incorporated in an oligomer (oligonucleotide) has the general formula I

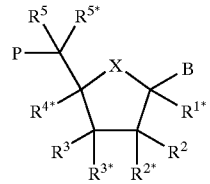

I wherein X is selected from —O— (the furanose motif), —S—, —N($R^{N*}$)—, —C($R^6R^{6*}$)—, —O—C($R^7R^{7*}$)—, —C($R^6R^{6*}$)—O—, —S—C($R^7R^{7*}$)—, —C($R^6R^{6*}$)—S—, —N($R^{N*}$)—C($R^7R^{7*}$)—, —C($R^6R^6$)—N($R^{N*}$)—, and —C($R^6R^{6*}$)—C($R^7R^{7*}$)—, where $R^6$, $R^{6*}$, $R^7$, $R^{7*}$, and $R^{N*}$ are as defined further below. Thus, the LNAs incorporated in the oligomer may comprise an either 5- or 6-membered ring as an essential part of the bi-, tri-, or polycyclic structure. It is believed that 5-membered rings (X=—O—, —S—, —N($R^{N*}$)—, —C($R^6R^{6*}$)—) are especially interesting in that they are able to occupy essentially the same conformations (however locked by the introduction of one or more biradicals (see below)) as the native furanose ring of a naturally occurring nucleoside. Among the possible 5-membered rings, the situations where X designates —O—, —S—, and —N($R^{N*}$)— seem especially interesting, and the situation where X is —O— appears to be particularly interesting.

The substituent B may designate a group which, when the oligomer is complexing with DNA or RNA, is able to interact (e.g. by hydrogen bonding or covalent bonding or electronic interaction) with DNA or RNA, especially nucleobases of DNA or RNA. Alternatively, the substituent B may designate a group which acts as a label or a reporter, or the substituent B may designate a group (e.g. hydrogen) which is expected to have little or no interactions with DNA or RNA. Thus, the substituent B is preferably selected from hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4$,$N^4$-ethanocytosin, $N^6$,$N^6$-ethano-2,6-diaminopurine, 5-methylcytosine, 5-($C^3$–$C^6$)-alkynylcytosine, 5-fluorouracil, 5-bromouracil, pseudoiso-cytosine, 2-hydroxy-5-methyl-4-triazolopyridin, isocytosine, isoguanin, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

When used herein, the term "DNA intercalator" means a group which can intercalate into a DNA or RNA helix, duplex or triplex. Examples of functional parts of DNA intercalators are acridines, anthracene, quinones such as anthraquinone, indole, quinoline, isoquinoline, dihydroquinones, anthracyclines, tetracyclines, methylene blue, anthracyclinone, psoralens, coumarins, ethidium-halides, dynemicin, metal complexes such as 1,10-phenanthroline-copper, tris(4,7-diphenyl-1,10-phenanthroline)ruthenium-cobalt-enediynes such as calcheamicin, porphyrins, distamycin, netropcin, viologen, daunomycin. Especially interesting examples are acridines, quinones such as anthraquinone, methylene blue, psoralens, coumarins, and ethidium-halides.

In the present context, the term "photochemically active groups" covers compounds which are able to undergo chemical reactions upon irradiation with light. Illustrative examples of functional groups hereof are quinones, especially 6-methyl-1,4-naphtoquinone, anthraquinone, naphtoquinone, and 1,4-dimethyl-anthraquinone, diazirines, aromatic azides, benzophenones, psoralens, diazo compounds, and diazirino compounds.

In the present context "thermochemically reactive group" is defined as a functional group which is able to undergo thermochemically-induced covalent bond formation with other groups. Illustrative examples of functional parts thermochemically reactive groups are carboxylic acids, carboxylic acid esters such as activated esters, carboxylic acid halides such as acid fluorides, acid chlorides, acid bromide, and acid iodides, carboxylic acid azides, carboxylic acid hydrazides, sulfonic acids, sulfonic acid esters, sulfonic acid halides, semicarbazides, thiosemicarbazides, aldehydes, ketones, primary alkohols, secondary alkohols, tertiary alkohols, phenols, alkyl halides, thiols, disulphides, primary amines, secondary amines, tertiary amines, hydrazines, epoxides, maleimides, and boronic acid derivatives.

In the present context, the term "chelating group" means a molecule that contains more than one binding site and frequently binds to another molecule, atom or ion through more than one binding site at the same time. Examples of functional parts of chelating groups are iminodiacetic acid, nitrilotriacetic acid, ethylenediamine tetraacetic acid (EDTA), aminophosphonic acid, etc.

In the present context, the term "reporter group" means a group which is detectable either by itself or as a part of an detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are dansyl (5-dimethylamino)-1-naphthalenesulfonyl), DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (trademarks for Biological Detection Systems, Inc.), erytrosine, coumaric acid, umbelliferone, texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radioisotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectrometry), enzymes (such as peroxidases, alkaline phosphatases, β-galactosidases, and glucose oxidases), antigens, antibodies, haptens (groups which are able to combine with an antibody, but which cannot initiate an immune response by itself, such as peptides and steroid hormones), carrier systems for cell membrane penetration such as: fatty acid residues, steroid moieties (cholesteryl), vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, Ruthenium, Europium, Cy5, Cy3, etc.

In the present context "ligand" means something which binds. Ligands can comprise functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_1$–$C_{20}$ alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

It will be clear for the person skilled in the art that the above-mentioned specific examples under DNA intercalators, photochemically active groups, thermochemically active groups, chelating groups, reporter groups, and ligands correspond to the "active/functional" part of the groups in question. For the person skilled in the art it is furthermore clear that DNA intercalators, photochemically active groups, thermochemically active groups, chelating groups, reporter groups, and ligands are typically represented in the form M-K- where M is the "active/functional" part of the group in question and where K is a spacer through which the "active/functional" part is attached to the 5- or 6-membered ring. Thus, it should be understood that the group B, in the case where B is selected from DNA intercalators, photochemically active groups, thermochemically active groups, chelating groups, reporter groups, and ligands, has the form M-K-, where M is the "active/functional" part of the DNA intercalator, photochemically active group, thermochemically active group, chelating group, reporter group, and ligand, respectively, and where K is an optional spacer comprising 1–50 atoms, preferably 1–30 atoms, in particular 1–15 atoms, between the 5- or 6-membered ring and the "active/functional" part.

In the present context, the term "spacer" means a thermochemically and photochemically non-active distance-making group and is used to join two or more different moieties of the types defined above. Spacers are selected on the basis of a variety of characteristics including their hydrophobicity, hydrophilicity, molecular flexibility and length (e.g. see Hermanson et. al., "Immobilised Affinity Ligand Techniques", Academic Press, San Diego, Calif. (1992), p. 137-ff). Generally, the length of the spacers are less than or about 400 Å, in some applications preferably less than 100 Å. The spacer, thus, comprises a chain of carbon atoms optionally interrupted or terminated with one or more heteroatoms, such as oxygen atoms, nitrogen atoms, and/or sulphur atoms. Thus, the spacer K may comprise one or more amide, ester, amino, ether, and/or thioether functionalities, and optionally aromatic or mono/polyunsaturated hydrocarbons, polyoxyethylene such as polyethylene glycol, oligo/polyamides such as poly-β-alanine, polyglycine, polylysine, and peptides in general, oligosaccharides, oligo/polyphosphates. Moreover the spacer may consist of combined units thereof. The length of the spacer may vary, taking into consideration the desired or necessary positioning and spatial orientation of the "active/functional" part of the group in question in relation to the 5- or 6-membered ring. In particularly interesting embodiments, the spacer includes a chemically cleavable group. Examples of such chemically cleavable groups include disulphide groups cleavable under reductive conditions, peptide fragments cleavable by peptidases, etc.

In one embodiment of the present invention, K designates a single bond so that the "active/functional" part of the group in question is attached directly to the 5- or 6-membered ring.

It will also be understood that the variations within the group B will offer the possibility for introducing mass differentiation between to oligomers which are constituted by the same nucleotides, but with different sequences. As will be described herein, this offers the possibility of constructing an array of detector molecules which depending on mass will reveal the exact sequence.

In a preferred embodiment, however, the substituent B in the general formulae I and II is preferably selected from nucleobases, in particular from adenine, guanine, thymine, cytosine and urasil.

In the oligomers (formula I), P designates the radical position for an internucleoside linkage to a succeeding monomer, or a 5'-terminal group. The first possibility applies when the LNA in question is not the 5'-terminal "monomer", whereas the latter possibility applies when the LNA in question is the 5'-terminal "monomer". It should be understood (which also will be clear from the definition of internucleoside linkage and 5'-terminal group further below) that such an internucleoside linkage or 5'-terminal group may include the substituent $R^5$ (or equally applicable: the substituent $R^{5*}$) thereby forming a double bond to the group P. (5'-Terminal refers to the position corresponding to the 5' carbon atom of a ribose moiety in a nucleoside.)

On the other hand, an internucleoside linkage to a preceding monomer or a 3'-terminal group (P*) may originate from the positions defined by one of the substituents $R^2$, $R^{2*}$, $R^3$, and $R^{3*}$, preferably from the positions defined by one of the substituents $R^3$ and $R^{3*}$. Analogously, the first possibility applies where the LNA in question is not the 3'-terminal "monomer", whereas the latter possibility applies when the LNA in question is the 3'-terminal "monomer". (3'-Terminal refers to the position corresponding to the 3' carbon atom of a ribose moiety in a nucleoside.)

In the present context, the term "monomer" relates to naturally occurring nucleosides, non-naturally occurring nucleosides, PNA monomers, etc. as well as LNAs. Thus, the term "succeeding monomer" relates to the neighbouring monomer in the 5'-terminal direction and the "preceding monomer" relates to the neighbouring monomer in the 3'-terminal direction. Such succeeding and preceding monomers, seen from the position of an LNA monomer, may be naturally occurring nucleosides or non-naturally occurring nucleosides, or even further LNA monomers.

Consequently, in the present context (as can be derived from the definitions above), the term "oligomer" means an oligonucleotide modified by the incorporation of one or more LNA(s).

The crucial part of the present invention is the presence of one or more rings fused to the 5- or 6-membered ring illustrated with the general formula I. Thus, one or two pairs of non-geminal substituents selected from the present substituents of $R^{1*}$, $R^{4*}$, $R^5$, $R^{5*}$, $R^6$, $R^{6*}$, $R^7$, $R^{7*}$, $R_{N*}$, and the ones of $R^2$, $R^{2*}$, $R^3$, and $R^{3*}$ not designating P* each designates a biradical consisting of 1–8 groups/atoms, preferably 1–4 groups/atoms, independently selected from —C($R^a R^b$)—, —C($R^a$)=C($R^a$)—, —C($R^a$)=N—, —O—, —Si($R^a$)$_2$—, —S—, —SO$_2$—, —N($R^a$)—, and >C=Z. (The term "present" indicates that the existence of some of the substituents, i.e. $R^6$, $R^{6*}$, $R^7$, $R^{7*}$, $R^{N*}$, is dependent on whether X includes such substituents.)

In the groups constituting the biradical(s), Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands (where the latter groups may include a spacer as defined for the substituent B), where aryl and heteroaryl may be optionally substituted. Moreover, two geminal substituents $R^a$ and $R^b$ together may designate optionally substituted methylene (=CH$_2$ optionally substituted one or two times with substituents as defined as optional substituents for aryl), and two non-geminal or geminal substituents selected from $R^a$, $R^b$, and any of the substituents $R^{1*}$, $R^2$, $R^{2*}$, $R^3$, $R^{3*}$, $R^{4*}$, $R^6$, $R^{5*}$, $R^6$ and $R^{6*}$, $R^7$, and $R^{7*}$ which are present and not involved in P, P* or the biradical(s) may together form an associated biradical selected from biradicals of the same kind as defined before. It will be clear that each of the pair(s) of non-geminal substituents thereby forms a mono- or bicyclic entity together with (i) the atoms to which the non-geminal substituents are bound and (ii) any intervening atoms.

It is believed that biradicals which are bound to the ring atoms of the 5- or 6-membered rings are preferred in that inclusion of the substituents $R^5$ and $R^{5*}$ may cause an undesired sterical interaction with internucleoside linkage. Thus, it is preferred that the one or two pairs of non-geminal substituents, which are constituting one or two biradical(s), respectively, are selected from the present substituents of $R^{1*}$, $F^{4*}$, $R^6$, $R^{6*}$, $R^7$, $R^{7*}$, $R^{N*}$, and the ones of $R^2$, $R^{2*}$, $R^3$, and $R^{3*}$ not designating P*.

Preferably, the LNAs incorporated in the oligomers comprise only one biradical constituted by a pair of (two) non-geminal substituents. In particular, it is preferred that $R^{3*}$ designates P* and that the biradical is formed between $R^{2*}$ and $R^{4*}$ or $R^2$ and $R^3$.

In the present context, i.e. in the present description and claims, the orientation of the biradicals are so that the left-hand side represents the substituent with the lowest number and the right-hand side represents the substituent with the highest number, thus, when $R^3$ and $R^5$ together designate a biradical "—O—CH$_2$—", it is understood that the oxygen atom represents $R^3$, thus the oxygen atom is e.g. attached to the position of $R^3$, and the methylene group represents $R^5$.

Considering the numerous interesting possibilities for the structure of the biradical(s) in LNA(s) incorporated in oligomers, it is believed that the biradical(s) constituted by pair(s) of non-geminal substituents preferably is/are selected from —(CR*R*)$_r$—Y—(CR*R*)$_s$—, —(CR*R*)$_r$—Y—(CR*R*)$_s$—,Y —Y—(CR*R*)$^{r*s}$—Y—, —Y—(CR*R*)$_r$—Y—(CR*R*)$_s$—, —(CR*R*)$_{r*s}$—, —Y—, —Y—Y—, wherein each Y is independently selected from —O—, —S—, —Si(R*)$_2$—, —N(R*)—, >C=O, —C(=O)—N(R*)—, and —N(R*)—C(=O)—, each R* is independently selected from hydrogen, halogen, azido, cyano, nitro, hydroxy, mercapto, amino, mono- or di(C$_{1-6}$-alkyl)amino, optionally substituted C$_{1-6}$-alkoxy, optionally substituted C$_{1-6}$-alkyl, DNA intercalators, photochemically active groups, thermochemically active groups, chelating groups, reporter groups, and ligands, and/or two adjacent (non-geminal) R* may together designate a double bond; and each of r and s is 0–4 with the proviso that the sum r*s is 1–5. Particularly interesting situations are those wherein each biradical is independently selected from —Y—, —(CR*R*)$_{r*s}$—, —(CR*R*)$_r$—Y—(CR*R*)$_s$—, and —Y—(CR*R*)$_{r*s}$—Y—, wherein and each of r and s is 0–3 with the proviso that the sum r*s is 1–4.

Considering the positioning of the biradical in the LNA(s), it is believed that the following situations are especially interesting, namely where: R$^{2*}$ and R$^{4*}$together designate a biradical selected from —Y—, —(CR*R*)r*s*1—, —(CR*R*)$_r$—Y—(CR*R*)$_s$—, and —Y—(CR*R*)$_{r*s}$—Y—; R$^2$ and R$^3$ together designate a biradical selected from —Y—, —(CR*R*)$_{r*s}$—, —(CR*R*)$_r$—Y—(CR*R*)$_s$—, and —Y—(CR*R*)$_{r*s}$—Y—; R$^{2*}$ and R$^3$ together designate a biradical selected from —Y—, —(CR*R*)$_{r*s}$—, —(CR*R*)$_r$—Y—(CR*R*)$_s$—, and —Y—(CR*R*)$_{r*s}$—Y—; R$^3$ and R$^{4*}$ together designate a biradical selected from —Y—, —(CR*R*)$_{r*s}$—, —(CR*R*)$_r$——Y—(CR*R*)$_{r*s}$—Y—; R$^3$ and R$^5$ together designate a biradical selected from —Y'—, —(CR*R*)$_{r*s*1}$—, —(CR*R*)$_r$—Y—(CR*R*)$_s$—, and —Y—(CR*R*)$_{r*s-Y-}$; R$^{1*}$ and R$^{4*}$ together designate a biradical selected from —Y'—, —(CR*R*)$_{r*s*1}$—, —(CR*R*)$_r$—Y—(CR*R*)$_s$—, and —Y—(CR*R*)$_{r*s}$—NR*—; or where R$^{1*}$ and R$^{2*}$ together designate a biradical selected from —Y—, —(CR*R*)$_{r*s}$—, —(CR*R*)$_r$—Y—(CR*R*)$_s$—, and —Y—(CR*R*)$_{r*s}$—Y—; wherein each of r and s is 0–3 with the proviso that the sum r*s is 1–4, Y is as defined above, and where Y' is selected from —NR*—C(=O)— and —C(=O)—NR*—. In these instances, R$^{3*}$ is preferably P*.

Particularly interesting oligomers are those wherein one of the following criteria applies for at least one LNA in an oligomer: R$^{2*}$ and R$^{4'}$ together designate a biradical selected from —O—, —S—, —N(R*)—, —(CR*R*)$_{r*s*1}$—, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r*s}$—O—, —S—(CR*R*)$_{r*s}$——O—, —O—(CR*R*)$_{r*s}$—S—, —N(R*)—(CR*R*)$_{r*s}$—O—, —O—(CR*R*)$_{r*s}$—N(R*)—, —S—(CR*R*)$_{r*s}$—, —N(R*)—(CR*R*)$_{r*s}$—N(R*)—, —N(R*)—(CR*R*)$_{r*s}$—S—, and —S—(CR*R*)$_{r*s}$—N(R*)—; R$^2$ and R$^3$ together designate a biradical selected from —O—, —(CR*R*)$_{r*s}$—, —(CR*R*)$_r$—O—(CR*R*)$_s$—, —(CR*R*)$_r$—S—(CR*R*)$_s$—, and —(CR*R*)$_r$—N(R*)—(CR*R*)$_s$—; R$^{2*}$ and R$^3$ together designate a biradical selected from —O—, —(CR*R*)$_{r*s}$—, —(CR*R*)$_r$—O—(CR*R*)$_s$—, —(CR*R*)$_r$—S—(CR*R*)$_s$—, and —(CR*R*)$_r$—N(R*)—(CR*R*)$_s$—; R$^3$ and R$^{4*}$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—; R$^3$ and R$^5$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—; R$^{1*}$ and R$^{4*}$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR R')$_s$—; or R$^{1*}$ and R$^{2*}$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—; wherein each of r and s is 0–3 with the proviso that the sum r*s is 1–4, and where RH designates hydrogen or C$_{1-4}$-alkyl. In these instances, R$^{3*}$ is preferably P*.

It is furthermore preferred that one R* is selected from hydrogen, hydroxy, optionally substituted C$_{1-6}$-alkoxy, optionally substituted C$_{1-6}$-alkyl, DNA intercalators, photochemically active groups, thermochemically active groups, chelating groups, reporter groups, and ligands, and any remaining substituents R* are hydrogen.

In one preferred embodiment, one group R* in the biradical of at least one LNA is selected from DNA intercalators, photochemically active groups, thermochemically active groups, chelating groups, reporter groups, and ligands (where the latter groups may include a spacer as defined for the substituent B).

With respect to the substituents R$^{1*}$, R$^2$, R$^{2*}$, R$^3$, R$^{4*}$, R$^5$, R$^{5*}$, R$^6$ and R$^{6*}$, R$^7$, and R7*, which are present and not involved in P, P* or the biradical(s), these are independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkylcarbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands (where the latter groups may include a spacer as defined for the substituent B), where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(NR$^N$) where R$^N$ is selected from hydrogen and C$_{1-4}$-alkyl, and where two adjacent (non-geminal) substituents may designate an additional bond resulting in a double bond; and R$^N$, when present and not involved in a biradical, is selected from hydrogen and C$_{1-4}$-alkyl.

Preferably, each of the substituents R$^{1*}$, R$^2$, R$^{2*}$, R$^3$, R$^{3*}$, R$^{4*}$, R$^5$, R$^{5*}$, R$^6$, R$^{6*}$, R$^7$, and R$^{7*}$, of the LNA(s), which are present and not involved in P, P* or the biradical(s), is independently selected from hydrogen, optionally substituted C$_{1-6}$-alkyl, optionally substituted C$_{1-6}$-alkenyl, hydroxy, C$_{1-6}$-alkoxy, C$_{1-6}$-alkenyloxy, carboxy, C$_{1-6}$-alkoxycarbonyl, C$_{1-6}$-alkylcarbonyl, formyl, amino, mono- and di(C$_{1-6}$-alkyl)amino, carbamoyl, mono- and di(C$_{1-6}$-alkyl)-amino-carbonyl, C$_{1-6}$-alkyl-carbonylamino, carbamido, azido, C$_{1-6}$-alkanoyloxy, sulphono, sulphanyl, C$_{1-6}$-alkylthio, DNA intercalators, photochemically active groups, thermochemically active groups, chelating groups, reporter groups, and ligands, and halogen, where two geminal substituents together may designate oxo, and where $R^N$, when present and not involved in a biradical, is selected from hydrogen and $C_{1-4}$-alkyl.

In a preferred embodiment of the present invention, X is selected from —O—, —S—, and —$NR^N$—, in particular —O—, and each of the substituents $R^{1*}$, $R^2$, $R^{2*}$, $R^3$, $R^{3*}$, $R^{4*}$, $R^5$, $R^{5*}$, $R^6$, $R^{6*}$, $R^7$, and $R^{7*}$ of the LNA(s), which are present and not involved in P, P* or the biradical(s), designate hydrogen.

In an even more preferred embodiment of the present invention, $R^{2*}$ and $R^4$ of an LNA incorporated into an oligomer together designate a biradical. Preferably, X is O, $R^2$ selected from hydrogen, hydroxy, and optionally substituted $C_{1-6}$-alkoxy, and $R^{1*}$, $R^3$, $R^5$, and $R^{5*}$ designate hydrogen, and, more specifically, the biradical is selected from —O—, —$(CH_2)_{0-1}$—O—$(CH_2)_{1-3}$—, —$(CH_2)_{0-1}$—S—$(CH_2)_{1-3}$—, —$(CH_2)_{0-1}$—N($R^N$)—$(CH_2)_{1-3}$—, and —$(CH_2)_{2-4}$—, in particular from —O—$CH_2$—, —S—$CH_2$—, and —$NR^H$—$CH_2$—. Generally, with due regard to the results obtained so far, it is preferred that the biradical constituting $R^{2*}$ and $R^{4*}$ forms a two atom bridge, i.e. the biradical forms a five membered ring with the furanose ring (X=O).

Particularly interesting LNA modified oligonucleotide are those where $R^{2*}$ and $R^{4*}$ of an incorporated LNA of formula Ia together designate a biradical selected from —O—$CH_2$—, —S—$CH_2$—, and —$NR^H$—$CH_2$—; X is O, B designates a nucleobase selected from adenine, guanine, thymine, cytosine and urasil; $R^2$ is hydrogen, and $R^{1*}$, $R^3$, $R^6$, and $R^{5*}$ designate hydrogen.

In another embodiment of the present invention, $R^2$ and $R^3$ of an LNA incorporated into an oligomer together designate a biradical. Preferably, X is O, $R^{2*}$ is selected from hydrogen, hydroxy, and optionally substituted $C_{1-6}$-alkoxy, and $R^{1*}$, $R^{4*}$, $R^5$, and $R^{5*}$ designate hydrogen, and, more specifically, the biradical is selected from —$(CH_2)_{0-1}$—O—$(CH_2)_{1-3}$—, —$(CH_2)^{0-1}$—S—$(CH_2)_{1-3}$—, —$(CH_2)_{0-1}$—N$(R^H)$—$(CH_2)_{1-3}$— and —$(CH_2)_{1-4}$—, in particular from —O—$CH_2$—, —S—$CH_2$—, —$N(R^H)$—$CH_2$—. In the latter case, the amino and thio variants appears to be particularly interesting.

In a further embodiment of the present invention, $R^{2*}$ and $R^3$ of an LNA incorporated into an oligomer together designate a biradical. Preferably, X is O, $R^2$ is selected from hydrogen, hydroxy, and optionally substituted $C_{1-6}$-alkoxy, and $R^{1*}$, $R^{4*}$, $R^5$, and $R^{5*}$ designate hydrogen, and, more specifically, the biradical is selected from —$(CH_2)_{0-1}$—O—$(CH_2)_{1-3}$—and —$(CH_2)_{2-4}$—.

In a further embodiment of the present invention, $R^3$ and $R^{4*}$ of an LNA incorporated into an oligomer together designate a biradical. Preferably, X is O, $R^{2*}$ selected from hydrogen, hydroxy, and optionally substituted $C_{1-6}$-alkoxy, and $R^{1*}$, $R^2$, $R^5$, and $R^{5*}$ designate hydrogen, and, more specifically, the biradical is —$(CH_2)_{0-2}$—O—$(CH_2)_{0-2}$—.

In a further embodiment of the present invention, $R^3$ and $R^{5*}$ of an LNA incorporated into an oligomer together designate a biradical. Preferably, X is O, $R^{2*}$ selected from hydrogen, hydroxy, and optionally substituted $C_{1-6}$-alkoxy, and $R^{1*}$, $R^2$, $R^4$, and $R^5$ designate hydrogen, and, more specifically, the biradical is selected from —O—$(CHR^*)_{2-3}$—and —$(CHR^*)_{1-3}$—O—$(CHR^*)_{0-3}$—.

In a further embodiment of the present invention, $R^{1*}$ and $R^{4*}$ of an LNA incorporated into an oligomer together designate a biradical. Preferably, X is O, $R^{2*}$ selected from hydrogen, hydroxy, and optionally substituted $C_{1-6}$-alkoxy, and $R^2$, $R^3$, $R^5$, and $R^{5*}$ designate hydrogen, and, more specifically, the biradical is —$(CH_2)_{0-2}$—O—$(CH_2)_{0-2}$—.

In these embodiments, it is furthermore preferred that at least one LNA incorporated in an oligomer includes a nucleobase (substituent B) selected from adenine and guanine. In particular, it is preferred that an oligomer have LNA incorporated therein both include at least one nucleobase selected from thymine, urasil and cytosine and at least one nucleobase selected from adenine and guanine. For LNA monomers, it is especially preferred that the nucleobase is selected from adenine and guanine.

For these interesting embodiments, it is also preferred that the LNA(s) has/have the general formula Ia (see below).

Within a variant of these interesting embodiments, all monomers of an oligonucleotide are LNA monomers.

As it will be evident from the general formula I (LNA(s)) in an oligomer) (and the general formula II (monomeric LNA)—see below) and the definitions associated therewith, there may be one or several asymmetric carbon atoms present in the oligomers (and monomeric LNAs) depending on the nature of the substituents and possible biradicals, cf. below. The oligomers prepared according to the method of the invention, as well as the oligomers per se, are intended to include all stereoisomers arising from the presence of any and all isomers of the individual monomer fragments as well as mixtures thereof, including racemic mixtures. When considering the 5- or 6-membered ring, it is, however, believed that certain stereochemical configurations will be especially interesting, e.g. the following

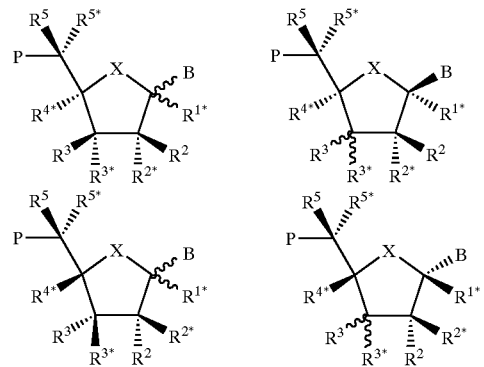

where the wavy lines represent the possibility of both diastereomers arising from the interchange of the two substituents in question.

An especially interesting stereoisomeric representation is the case where the LNA(s) has/have the following formula Ia

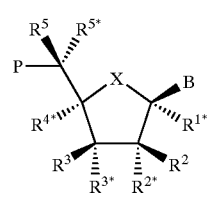

Ia

Also interesting as a separate aspect of the present invention is the variant of formula Ia where B is in the "α-configuration".

In these cases, as well as generally, $R^{3*}$ preferably designates P*.

The oligomers according typically comprise 1–10000 LNA(s) of the general formula I (or of the more detailed general formula Ia) and 0–10000 nucleosides selected from naturally occurring nucleosides and nucleoside analogues. The sum of the number of nucleosides and the number of LNA(s) is at least 2, preferably at least 3, in particular at least 5, especially at least 7, such as in the range of 2–15000, preferably in the range of 2–100, such as 3–100, in particular in the range of 2–50, such as 3–50 or 5–50 or 7–50.

Preferably at least one LNA comprises a nucleobase as the substituent B.

In the present context, the term "nucleoside" means a glycoside of a heterocyclic base. The term "nucleoside" is used broadly as to include non-naturally occurring nucleosides, naturally occurring nucleosides as well as other nucleoside analogues. Illustrative examples of nucleosides are ribonucleosides comprising a ribose moiety as well as deoxyribonuclesides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

When considering the definitions and the known nucleosides (naturally occurring and non-naturally occurring) and nucleoside analogues (including known bi- and tricyclic analogues), it is clear that an oligomer may comprise one or more LNA(s) (which may be identical or different both with respect to the selection of substituent and with respect to selection of biradical) and one or more nucleosides and/or nucleoside analogues. In the present context "oligonucleotide" means a successive chain of nucleosides connected via internucleoside linkages, however, it should be understood that a nucleobase in one or more nucleotide units (monomers) in an oligomer (oligonucleotide) may have been modified with a substituent B as defined above.

The oligomers may be linear, branched or cyclic. In the case of a branched oligomer, the branching points may be located in a nucleoside, in an internucleoside linkage or, in an intriguing embodiment, in an LNA. It is believed that in the latter case, the substituents $R^2$, $R^{2*}$, $R^3$, and $R^{3*}$ may designate two groups P* each designating an internucleoside linkage to a preceding monomer, in particular, one of $R^2$ and $R^{2*}$ designate P* and one or $R^3$ and $R^{3*}$ designate a further P*.

As mentioned above, the LNA(s) of an oligomer are connected with other monomers via an internucleoside linkage. In the present context, the term "internucleoside linkage" means a linkage consisting of 2 to 4, preferably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where $R^H$ is selected form hydrogen and $C_{1-4}$-alkyl, and R" is selected from $C_{1-6}$-alkyl and phenyl. Illustrative examples of such internucleoside linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—, —O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—, —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—$NR^H$—, —$NR^H$—P(O)$_2$—O—, —O—P(O,$NR^H$)—O—, —$CH_2$—P(O)$_2$—O—, —O—P(O)$_2$—$CH_2$—, and —O—Si(R")$_2$—O—; among which —$CH_2$—CO—$NR^H$—, —$CH_2NR^H$—O—, —S—$CH_2$—O—, —O—P(O)$_2$—O—, —O—P(O,S)—O—, —O—P(S)$_2$—O—, —$NR^H$—P(O)$_2$—O—, —O—P(O,$NR^H$)—O—, —O—PO(R")—O—, —O—PO(CH$_3$)—O—, and —O—PO(NHR$^N$)—O—, where $R^H$ is selected form hydrogen and $C_{1-4}$-alkyl, and R" is selected from $C_{1-6}$-alkyl and phenyl, are especially preferred. Further illustrative examples are given in Mesmaeker et. al., Current Opinion in Structural Biology 1995, 5, 343–355. The left-hand side of the internucleoside linkage is bound to the 5- or 6-membered ring as substituent P*, whereas the right-hand side is bound to the 5'-position of a preceding monomer.

It is also clear from the above that the group P may also designate a 5'-terminal group in the case where the LNA in question is the 5'-terminal monomer. Examples of such 5'-terminal groups are hydrogen, hydroxy, optionally substituted $C_{1-6}$-alkyl, optionally substituted $C_{1-6}$-alkoxy, optionally substituted $C_{1-6}$-alkylcarbonyloxy, optionally substituted aryloxy, monophosphate, diphosphate, triphosphate, and —W—A', wherein W is selected from —O—, —S—, and —N($R^H$)— where $R^H$ is selected from hydrogen and $C_{1-6}$-alkyl, and where A' is selected from DNA intercalators, photochemically active groups, thermochemically active groups, chelating groups, reporter groups, and ligands (where the latter groups may include a spacer as defined for the substituent B).

In the present description and claims, the terms "monophosphate", "diphosphate", and "triphosphate" mean groups of the formula: —O—P(O)$_2$—O$^-$, —O—P(O)$_2$—O—P(O)$_2$—O$^-$, and —O—P(O)$_2$—O—P(O)$_2$—O—P(O)$_2$—O$^-$, respectively.

In a particularly interesting embodiment, the group P designates a 5'-terminal groups selected from monophosphate, diphosphate and triphosphate. Especially the triphosphate variant is interesting as a substrate for nucleic acid polymerases.

Analogously, the group P*may designate a 3'-terminal group in the case where the LNA in question is the 3'-terminal monomer. Examples of such 3'-terminal groups are hydrogen, hydroxy, optionally substituted $C_{1-6}$-alkoxy, optionally substituted $C_{1-6}$-alkylcarbonyloxy, optionally substituted aryloxy, and —W—A', wherein W is selected from——O—, —S—, and —N($R^H$) where $R^H$ is selected from hydrogen and $C_{1-6}$-alkyl, and where A' is selected from DNA intercalators, photochemically active groups, thermochemically active groups, chelating groups, reporter groups, and ligands (where the latter groups may include a spacer as defined for the substituent B).

In a preferred embodiment of the present invention, the oligomer has the following formula V:

$$G\text{-}[Nu\text{-}L]_{n(0)}\text{-}\{[LNA\text{-}L]_{m(q)}\text{-}[Nu\text{-}L]_{n(q)}\}_q\text{-}G^* \quad\quad V$$

wherein q is 1–50;

each of n(0), . . . , n(q) is independently 0–10000;

each of m(1), . . . , m(q) is independently 1–10000;

with the proviso that the sum of n(0), . . . , n(q) and m(1), . . . , m(q) is 2–15000;

G designates a 5'-terminal group;

each Nu independently designates a nucleoside selected from naturally occurring nucleosides and nucleoside analogues;

each LNA independently designates a nucleoside analogue; each L independently designates an internucleoside linkage between two groups selected from Nu and LNA, or L together with G* designates a 3'-terminal group; and each LNA-L independently designates a nucleoside analogue of the general formula I as defined above, or preferably of the general formula Ia as defined above.

The construction of the LNA modified oligomers used in the present invention depends on the function, i.e. whether the LNA modified oligonucleotide is to be used, e.g., as a capture probe, which is not to be analysed by mass spectrometry, or whether the LNA modified oligonucleotide is to be used as the oligomer to be analysed by mass spectrometry.

In the first instance (capture probe), the degree of LNA modification might be low in that the number of LNAs in the LNA modified oligonucleotide should just ensure that the hybridisation between the target nucleic acid and the LNA modified oligonucleotide is sufficiently stable, i.e. more stable that by using an unmodified oligonucleotide. Such LNA modified oligonucleotide might, thus, be relatively long, e.g. 10–200 nucleotides long, and in this instance, the LNA modified oligonucleotide might include a domain of, e.g. 2–15 LNAs/nucleotides for hybridisation to the target nucleic acid and a further domain primarily constituted by nucleotides (e.g. a 2–200 base DNA) for spacing and immobilisation to a solid support. Thus, with reference to formula V, an example would be: q is 1, and n(0) or n(1) is 1–200, preferable 2–50 such as 2–20, and the other of n(0) and n(1) is 0, m(1) is 1–50 such as 2–20 or 3–15. In this instance, the "long" oligonucleotide typically comprises a ratio of LNAs to nucleotides in the oligonucleotide of 1:20 to 1:1, such as 1:10 to 1:2, e.g. 1:8 to 1:4.

In the second instance (mass spectrometry analysable probe), the degree of LNA modification is typically relatively high (see below) and the LNA modified oligonucleotide is relatively short, e.g. 2–30 LNAs/nucleotides long, due to the fact that the resolution of the mass spectrometry signal decreases with increasing length (molecular mass). In this instance, the "short" oligonucleotide typically comprises a ratio of LNAs to nucleotides in the oligonucleotide of at least 1:2, such as at least 1:1, preferably at least 2:1.

Within the above-mentioned embodiments, as well as generally, the present invention provides the intriguing possibility of including LNAs in oligonucleotides with different nucleobases (and thereby different molecular masses), in particular both nucleobases selected from thymine, cytosine and urasil and nucleobases selected from adenine and guanine.

The oligomer may further comprises a PNA mono- or oligomer segment of the formula

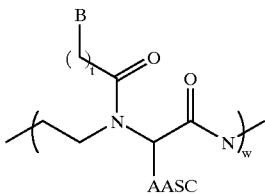

wherein B is a defined above for the formula I, AASC designates hydrogen or an amino acid side chain, t is 1–5, and w is 1–50.

In the present context, the term "amino acid side chain" means a group bound to the α-atom of an α-amino acids, i.e. corresponding to the α-amino acid in question without the glycine moiety, preferably an either naturally occurring or a readily available α-amino acid. Illustrative examples are hydrogen (glycine itself), deuterium (deuterated glycine), methyl (alanine), cyanomethyl (β-cyano-alanine), ethyl, 1-propyl (norvaline), 2-propyl (valine), 2-methyl-1-propyl (leucine), 2-hydroxy-2-methyl-1-propyl (β-hydroxy-leucine), 1-butyl (norleucine), 2-butyl (isoleucine), methylthioethyl (methionine), benzyl (phenyl-alanine), p-amino-benzyl (p-amino-phenylalanine), p-iodo-benzyl (p-iodo-phenylalanine), p-fluoro-benzyl (p-fluoro-phenylalanine), p-bromo-benzyl (p-bromo-phenylalanine), p-chloro-benzyl (p-chloro-phenylalanine), p-nitro-benzyl (p-nitro-phenylalanine), 3-pyridylmethyl (β-(3-pyridyl)-alanine), 3,5-diiodo-4-hydroxy-benzyl (3,5-diiodo-tyrosine), 3,5-dibromo-4-hydroxy-benzyl (3,5-dibromo-tyrosine), 3,5-dichloro-4-hydroxy-benzyl (3,5-dichloro-tyrosine), 3,5-difluoro-4-hydroxy-benzyl (3,5-difluoro-tyrosine), 4-methoxy-benzyl (O-methyl-tyrosine), 2-naphtylmethyl (β-(2-naphtyl)-alanine), 1-naphtylmethyl (β-(1-naphtyl)-alanine), 3-indolylmethyl (tryptophan), hydroxymethyl (serine), 1-hydroxyethyl (threonine), mercaptomethyl (cysteine), 2-mercapto-2-propyl (penicillamine), 4-hydroxy-benzyl (tyrosine), aminocarbonylmethyl (asparagine), 2-aminocarbonylethyl (glutamine), carboxymethyl (aspartic acid), 2-carboxyethyl (glutamic acid), aminomethyl (α,β-diamino-propionic acid), 2-aminoethyl (α,γ-diaminobutyric acid), 3-amino-propyl (ornithine), 4-amino-1-butyl (lysine), 3-guanidino-1-propyl (arginine), and 4-imidazolylmethyl (histidine).

PNA mono- or oligomer segment may be incorporated in a oligomer as described in EP 0672677 A2.

The otigomers are also intended to cover chimeric oligomers. "Chimeric oligomers" means two or more oligomers with monomers of different origin joined either directly or via a spacer. Illustrative examples of such oligomers which can be combined are peptides, PNA-oligomers, oligomers containing LNAs, and oligonucleotide oligomers.

Apart from the oligomers defined above, the present invention also utilises monomeric LNAs (preferably triphosphates) as substrates for, e.g., nucleic acid polymerases, polynucleotide kinases, and as terminal transferases. The monomeric LNAs correspond in the overall structure (especially with respect to the possible biradicals) to the LNAs defined as constituents in oligomers, however with respect to the groups P and P* the monomeric LNAs differ slightly as will be explained below. Furthermore, the monomeric LNAs may comprise functional group protecting groups, especially in the cases where the monomeric LNAs are to be incorporated into oligomers by chemical synthesis.

An interesting subgroup of the possible monomeric LNAs comprises bicyclic nucleoside analogues (LNAs) of the general formula II

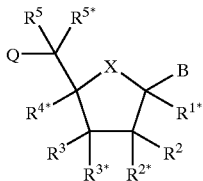

wherein the substituent B is selected from nucleobases, DNA intercalators, photochemically active groups, thermochemically active groups, chelating groups, reporter groups, and ligands; X is selected from —O—, —S—, —N($R^{N*}$)—, and —C($R^6R^{6*}$)—, preferably from —O—, —S—, and —N($R^{N*}$)—; one of the substituents $R^2$, $R^{2*}$, $R^3$, and $R^{3*}$ is a group Q*;

each of Q and Q* is independently selected from hydrogen, azido, halogen, cyano, nitro, hydroxy, Prot-O—, Act-O—, mercapto, Prot-S—, Act-S—, $C_{1-6}$-alkylthio, amino, Prot-N($R^H$)—, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, Act-O—$CH_2$—, aminomethyl, Prot-N($R^H$)—$CH_2$—, Act-N($R^H$)—$CH_2$—, carboxymethyl, sulphonomethyl, where Prot is a protection group for —OH, —SH, and —NH($R^H$), respectively, Act is an activation group for —OH, —SH, and —NH($R^H$), respectively, and $R^H$ is selected from hydrogen and $C_{1-6}$-alkyl;

$R^{2*}$ and $R^{4*}$ together designate a biradical selected from —O—, —S—, —N(R*)—, —(CR*R*)$_{r*s*1}$—, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r*s}$—, O—, —S—(CR*R*)$_{r*s}$—O—, —O—(CR*R*)$_{r*s}$—S—, —N(R*)—(CR*R*)$_{r*s}$—O—, —O—(CR*R*)$_{r*s}$—N(R*)—, —S—(CR*R*)$_{r*s}$—S—, —N(R*)—(CR*R*)$_{r*s}$—N(R*)—, —N(R*)—(CR*R*)$_{r*s}$—S—, and —S—(CR*R*)$_{r*s}$—N(R*)—; $R^2$ and $R^3$ together designate a biradical selected from —O—, —(CR*R*)$_{r*s}$—, —(CR*R*)$_r$—O—(CR*R*)$_s$—, —(CR*R*)$_r$—S—(CR*R*)$_s$—, and —(CR*R*)$_r$—N(R*)—(CR*R*)$_s$—; $R^{2*}$ and $R^3$ together designate a biradical selected from —O—, —(CR*R*)$_{r*s}$—, —(CR*R*)$_r$—O—(CR*R*)$_s$—, —(CR*R*)$_r$—S—(CR*R*)$_s$—, and —(CR*R*)$_r$—N(R*)—(CR*R*)$_s$—; $R^3$ and $R^{4*}$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—; $R^3$ and $R^5$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—; $R^{1*}$ and $R^{4*}$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—; or $R^{1*}$ and $R^{2*}$ together designate a biradical selected from —(CR*R*)$_r$—O—(CR*R*)$_s$—, —(CR*R*)$_r$—S—(CR*R*)$_s$—, and —(CR*R*)$_r$—N(R*)—(CR*R*)$_s$—;

wherein R' is as defined above for the oligomers; and each of the substituents $R^{1*}$, $R^2$, $R^{2*}$, $R^3$, $R^{4*}$, $R^5$, and $R^{5*}$, which are not involved in Q, Q* or the biradical, are as defined above for the oligomers.

The monomeric LNAs also comprise basic salts and acid addition salts thereof. Furthermore, it should be understood that any chemical group (including any nucleobase), which is reactive under the conditions prevailing in chemical oligonucleotide synthesis, is optionally functional group protected as known in the art. This means that groups such as hydroxy, amino, carboxy, sulphono, and mercapto groups, as well as nucleobases, of a monomeric LNA are optionally functional group protected. Protection (and deprotection) is performed by methods known to the person skilled in the art (see, e.g., Greene, T. W. and Wuts, P. G. M., "Protective Groups in Organic Synthesis", 2$^{nd}$ ed., John Wiley, N.Y. (1991), and M. J. Gait, Oligonucleotide Synthesis, IRL Press, 1984).

In a preferred embodiment, the group B in a monomeric LNA is preferably selected from nucleobases and protected nucleobases, preferably nucleobases selected from adenine, guanine, cytosine, thymine and urasil.

In the monomeric LNAs, one of Q and Q*, preferably Q*, designates a group selected from Act-O—, Act-S—, Act-N($R^H$)—, Act-O—$CH_2$—, Act-S—$CH_2$—, Act-N($R^H$)—$CH_2$—, and the other of Q and Q*, preferably Q, designates a group selected from hydrogen, azido, halogen, cyano, nitro, hydroxy, Prot-O—, mercapto, Prot-S—, $C_{1-6}$-alkylthio, amino, Prot-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{1-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, aminomethyl, Prot-N($R^H$)—$CH_2$—, carboxymethyl, sulphonomethyl, and $R^H$ is selected from hydrogen and $C_{1-6}$-alkyl.

In the case described above, the group Prot designates a protecting group for —OH, —SH, and —NH($R^H$), respectively. Such protection groups are selected from the same as defined above for hydroxy protection groups, mercapto protection group, and amino protection groups, respectively, however taking into consideration the need for a stable and reversible protection group. However, it is preferred that any protection group for —OH is selected from optionally substituted trityl, such as dimethoxytrityl (DMT), monomethoxytrityl (MMT), and trityl, and 9-(9-phenyl) xanthenyl (pixyl), optionally substituted, tetrahydropyranyl (thp) (further suitable hydroxy protection groups for phosphoramidite oligonucleotide synthesis are described in Agrawal, ed. "Protocols for Oligonucleotide Conjugates"; Methods in Molecular Biology, vol. 26, Humana Press, Totowa, N.J. (1994) and Protocols for Oligonucleotides and Analogs, vol 20, (Sudhir Agrawal, ed.), Humana Press, 1993, Totowa, N.J.), or protected as acetal; that any protection group for —SH is selected from trityl, such as dimethoxytrityl (DMT), monomethoxytrityl (MMT), and trityl, and 9-(9-phenyl)xanthenyl (pixyl), optionally substituted, tetrahydropyranyl (thp) (further suitable mercapto protection groups for phosphoramidite oligonucleotide synthesis are also described in Agrawal (see above); and that any protecting group for —NH($R^H$) is selected from trityl, such as dimethoxytrityl (DMT), monomethoxytrityl (MMT), and trityl, and 9-(9-phenyl)xanthenyl (pixyl), optionally substituted, tetrahydropyranyl (thp) (further suitable amino protection groups for phosphoramidite oligonucleotide synthesis are also described in Agrawal (see above).

In the above, as well as for any monomeric LNAs defined herein, Act designates an activation group for —OH, —SH, and —NH($R^H$), respectively. Such activation groups are, e.g., selected from optionally substituted O-phosphoramidite, optionally substituted O-phosphortriester, optionally substituted O-phosphordiester, optionally substituted H-phosphonate, and optionally substituted O-phosphonate.

In the present context, the term "phosphoramidite" means a group of the formula —P($OR^x$)—N($R^y$)$_2$, wherein $R^x$ designates an optionally substituted alkyl group, e.g. methyl, 2-cyanoethyl, or benzyl, and each of $R^y$ designate optionally substituted alkyl groups, e.g. ethyl or isopropyl, or the group —N($R^y$)$_2$ forms a morpholino group (—N(CH$_2$CH$_2$)$_2$O). $R^x$ preferably designates 2-cyanoethyl and the two $R^y$ are preferably identical and designate isopropyl. Thus, an especially relevant phosphoramidite is N,N-diisopropyl-O-(2-cyanoethyl)phosphoramidite.

It should be understood that the protecting groups used herein for a single monomeric LNA or several monomeric LNAs may be selected so that when this/these LNA(s) are incorporated in an oligomer, it will be possible to perform either a simultaneous deprotection or a sequential deprotection of the functional groups. The latter situation opens for the possibility of regioselectively introducing one or several "active/functional" groups such as DNA intercalators, photochemically active groups, thermochemically active groups, chelating groups, reporter groups, and ligands, where such groups may be attached via a spacer as described above.

In a preferred embodiment, Q is selected from hydrogen, azido, halogen, cyano, nitro, hydroxy, Prot-O—, mercapto, Prot-S—, $C_{1-6}$-alkylthio, amino, Prot-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—CH$_2$—, aminomethyl, Prot-N($R^H$)—CH$_2$—, carboxymethyl, sulphonomethyl, where Prot is a protection group for —OH, —SH, and —NH($R^H$), respectively, and $R^H$ is selected from hydrogen and $C_{1-6}$-alkyl; and Q* is selected from hydrogen, azido, halogen, cyano, nitro, hydroxy, Act-O—, mercapto, Act-S—, $C_{1-6}$-alkylthio, amino, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, DNA intercalators, photochemically active groups, thermochemically active groups, chelating groups, reporter groups, ligands, carboxy, sulphono, where Act is an activation group for —OH, —SH, and —NH($R^H$), respectively, and $R^H$ is selected from hydrogen and $C_{1-6}$-alkyl.

The monomeric LNAs of the general formula II may, as the LNAs incorporated into oligomers, represent various stereoisomers. Thus, the stereochemical variants described above for the LNAs incorporated into oligomers are believed to be equally applicable in the case of monomeric LNAs (however, it should be noted that P should then be replaced with Q).

In a preferred embodiment, the monomeric LNA has the general formula IIa

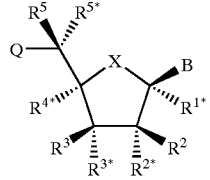

IIa wherein the substituents are defined as above.

Furthermore, with respect to the definitions of substituents, biradicals, R*, etc. the same preferred embodiments as defined above for the oligomer according to the invention also apply in the case of monomeric LNAs.

In a particularly interesting embodiment of the monomeric LNAs, B designates a nucleobase, preferably a nucleobase selected from thymine, cytosine, urasil, adenine and guanine (in particular adenine and guanine), X is —O—, $R^{2*}$ and $R^{4*}$ together designate a biradical selected from —(CH$_2$)$_{0-1}$—O—(CH$_2$)$_{1-3}$—, —(CH$_2$)$_{0-1}$—S—(CH$_2$)$_{1-3}$— and —(CH$_2$)$_{0-1}$—N($R^N$)—(CH$_2$)$_{1-3}$—, in particular —O—CH$_2$—, —S—CH$_2$— and —$R^N$—CH$_2$—, where $R^N$ is selected from hydrogen and $C_{1-4}$-alkyl, Q designates Prot-O—, $R^{3*}$ is Q* which designates Act-OH, and $R^{1*}$, $R^2$, $R^3$, $R^5$, and $R^{5*}$ each designate hydrogen. In this embodiment, $R^N$ may also be selected from DNA intercalators, photochemically active groups, thermochemically active groups, chelating groups, reporter groups and ligands.

In a further particularly interesting embodiment of the monomeric LNAs, B designates a nucleobase, preferably a nucleobase selected from thymine, cytosine, urasil, adenine and guanine (in particular adenine and guanine), X is —O—, $R^{2*}$ and $R^{4*}$ together designate a biradical selected from —(CH$_2$)$_{0-1}$—O—(CH$_2$)$_{1-3}$—, —(CH$_2$)$_{0-1}$—S—(CH$_2$)$_{1-3}$—, and —(CH$_2$)$_{0-1}$—N($R^N$)—(CH$_2$)$_{1-3}$—, in particular —O—CH$_2$—, —S—CH$_2$—and —$R^N$—CH$_2$—, where $R^N$ is selected from hydrogen and $C_{1-4}$-alkyl, Q is selected from hydroxy, mercapto, $C_{1-6}$-alkylthio, amino, mono- or di($C_{1-6}$-alkyl)amino, optionally substituted $C_{1-6}$-alkoxy, optionally substituted $C_{2-6}$-alkenyloxy, optionally substituted $C_{2-6}$-alkynyloxy, monophosphate, diphosphate, and triphosphate, $R^{3*}$ is Q*which is selected from hydrogen, azido, halogen, cyano, nitro, hydroxy, mercapto, $C_{1-6}$-alkylthio, amino, mono- or di($C_{1-6}$-alkyl)amino, optionally substituted $C_{1-6}$-aalkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, and optionally substituted $C_{2-6}$-alkynyloxy, $R^3$ is selected from hydrogen, optionally substituted $C_{1-6}$-alkyl, optionally substituted $C_{2-6}$-alkenyl, and optionally substituted $C_{2-6}$-alkynyl, and $R^{1*}$, $R^2$, $R^5$, and $R^{5*}$ each designate hydrogen. Also here, $R^N$ may also be selected from DNA LN intercalators, photochemically active groups, thermochemically active groups, chelating groups, reporter groups and ligands.

In a further particularly interesting embodiment of the monomeric LNAs of the present invention, B designates a nucleobase, X is —O—, $R^2$ and $R^3$ together designate a biradical selected from —(CH$_2$)$_{0-1}$—O—CH=CH—, —(CH$_2$)$_{0-1}$—S—CH=CH—, and —(CH$_2$)$_{0-1}$—N($R^N$)—CH=CH— where $R^N$ is selected from hydrogen and $C_{1-4}$-alkyl, Q is selected from hydroxy, mercapto, $C_{1-6}$-alkylthio, amino, mono- or di($C_{2-6}$-alkyl)amino, optionally substituted $C_{2-6}$-alkoxy, optionally substituted $C_{2-6}$-ralkenyloxy, optionally substituted $C_{2-6}$-alkynyloxy, monophosphate, diphosphate, and triphosphate, $R^{3*}$ is $Q^*$ which is selected from hydrogen, azido, halogen, cyano, nitro, hydroxy, mercapto, $C_{1-6}$-alkylthio, amino, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, and optionally substituted $C_{2-6}$-alkynyloxy, and $R^{1*}$, $R^{2*}$, $R^{4*}$, $R^5$, and $R^{5*}$ each designate hydrogen.

In a particularly interesting embodiment, the oligomer comprising at least one LNA of the general formula Ia

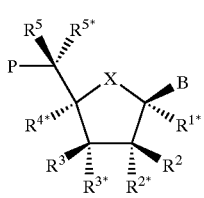

Ia wherein X is —O—; B is selected from nucleobases, DNA intercalators, photochemically active groups, thermochemically active groups, chelating groups, reporter groups, and ligands; P designates the radical position for an internucleoside linkage to a succeeding monomer, or a 5'-terminal group, such internucleoside linkage or 5'-terminal group optionally including the substituent $R^5$; $R^{3*}$ is a group $P^*$ which designates an internucleoside linkage to a preceding monomer, or a 3'-terminal group; $R^{2*}$ and $R^{4*}$ together designate a biradical selected from —O—, —S—, —N(R*)—, —(CR*R*)$_{r*s*1}$—, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r*s}$—O—, —S—(CR*R*)$_{r*s}$—O—, —O—(CR*R*)$_{r*s}$—S—, —N(R*)—(CR*R*)$_{r*s}$—O—, —O—(CR*R*)$_{r*s}$—N(R*)—, —S—(CR*R*)$_{r*s}$—S—, —N(R*)—(CR*R*)$_{r*s}$—N(R*)—, —N(R*)—(CR*R*)$_{r*s}$—S—, and —S—(CR*R*)$_{r*s}$—N(R*)—; wherein each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond, and each of r and s is 0–3 with the proviso that the sum r*s is 1–4; each of the substituents $R^{1*}$, $R^2$, $R^3$, $R^5$, and R* is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-amino-carbonyl, $C_{1-6}$-alkyl-carbonylamino, carbamido, azido, $C_{1-6}$-alkanoyloxy, sulphono, sulphanyl, $C_{1-6}$-alkylthio, DNA intercalators, photochemically active groups, thermochemically active groups, chelating groups, reporter groups, and ligands, and halogen, where two geminal substituents together may designate oxo; and basic salts and acid addition salts thereof. In particular, one R* is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen.

Especially, the biradical is selected from —O—, —(CH$_2$)$_{0-1}$—O—(CH$_2$)$_{1-3}$—, —(CH$_2$)$_{0-1}$—S—(CH$_2$)$_{1-3}$—, —(CH$_2$)$_{0-1}$—N(R$^N$)—(CH$_2$)$_{1-3}$—, and —(CH$_2$)$_{2-4}$—.

In a further particularly interesting embodiment, the present invention relates to an LNA of the general formula IIa

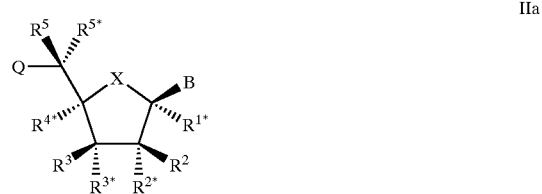

IIa wherein X is —O—; B is selected from nucleobases, DNA intercalators, photochemically active groups, thermochemically active groups, chelating groups, reporter groups, and ligands; $R^{3*}$ is a group $Q^*$; each of Q and $Q^*$ is independently selected from hydrogen, azido, halogen, cyano, nitro, hydroxy, Prot-O—, Act-O—, mercapto, Prot-S—, Act-S—, $C_{1-6}$-alkylthio, amino, Prot-N(R$^H$)—, Act-N(R$^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—CH$_2$—, Act-O—CH$_2$—, aminomethyl, Prot-N(R$^H$)—CH$_2$—, Act-N(R$^H$)—CH$_2$—, carboxymethyl, sulphonomethyl, where Prot is a protection group for —OH, —SH, and —NH(R$^H$), respectively, Act is an activation group for —OH, —SH, and —NH(R$^H$), respectively, and R$^H$ is selected from hydrogen and $C_{1-6}$-alkyl; $R^{2*}$ and $R^{4*}$ together designate a biradical selected from —O—, —S, —N(R*)—, —(CR*R*)$_{r*s*1}$—, —(CR*R*)$_r$—O—(CR*R*)$_s$—, —(CR*R*)$_r$—S—(CR*R*)$_r$—N(R*)—(CR*R*)$_s$—, —O—(CR*R*)$_{r*s}$—O—, —S—(CR*R*)$_{r*s}$—O—, —O—(CR*R*)$_{r*s}$—S—, —N(R*)—(CR*R*)$_{r*s}$—O—, —O—(CR*R*)$_{r*s}$—N(R*)—, —S—(CR*R*)$_{r*s}$—S—, —N(R*)—(CR*R*)$_{r*s}$—N(R*)—, —N(R*)—(CR*R*)$_{r*s}$—S—, and —S—(CR*R*)$_{r*s}$—N(R*)—; wherein each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond, and each of r and s is 0–3 with the proviso that the sum r*s is 1–4; each of the substituents $R^{1*}$, $R^2$, $R^3$, $R^5$, and $R^{5*}$ is independently selected from hydrogen, optionally substituted $C_{1-6}$-alkyl, optionally substituted $C_{1-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-amino-carbonyl, $C_{1-6}$-alkyl-carbonylamino, carbamido, azido, $C_{1-6}$-alkanoyloxy, sulphono, sulphanyl, $C_{1-6}$-alkylthio, DNA intercalators, photochemically active groups, thermochemically active groups, chelating groups, reporter groups, and ligands, and halogen, where two geminal substituents together may designate oxo; and basic salts and acid addition salts thereof; and with the proviso that any chemical group (including any nucleobase), which is reactive under the conditions prevailing in oligonucleotide synthesis, is optionally functional group protected. Preferably, one R* is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen. Especially, the biradical is selected from —O—, —(CH$_2$)$_{0-1}$—O—(CH$_2$)$_{1-3}$—, —(CH$_2$)$_{0-1}$—S—(CH$_2$)$_{1-3}$—, —(CH$_2$)$_{0-1}$—N(R$^N$)—(CH$_2$)$_{1-3}$—, and —(CH$_2$)$_{2-4}$—.

Definitions

In the present context, the term "$C_{1-12}$-alkyl" means a linear, cyclic or branched hydrocarbon group having 1 to 12 carbon atoms, such as methyl, ethyl, propyl, iso-propyl, cyclopropyl, butyl, tert-butyl, iso-butyl, cyclobutyl, pentyl, cyclopentyl, hexyl, cyclohexyl, and dodecyl. Analogously, the term "$C_{1-6}$-alkyl" means a linear, cyclic or branched hydrocarbon group having 1 to 6 carbon atoms, such as methyl, ethyl, propyl, iso-propyl, pentyl, cyclopentyl, hexyl, cyclohexyl, and the term "$C_{1-4}$-alkyl" is intended to cover linear, cyclic or branched hydrocarbon groups having 1 to 4 carbon atoms, e.g. methyl, ethyl, propyl, iso-propyl, cyclopropyl, butyl, iso-butyl, tert-butyl, cyclobutyl.

Preferred examples of "$C_{1-6}$-alkyl" are methyl, ethyl, propyl, iso-propyl, butyl, tert-butyl, iso-butyl, pentyl, cyclopentyl, hexyl, cyclohexyl, in particular methyl, ethyl, propyl, iso-propyl, tert-butyl, iso-butyl and cyclohexyl. Preferred examples of "$C_{1-4}$-alkyl" are methyl, ethyl, propyl, iso-propyl, butyl, tert-butyl, and iso-butyl.

Similarly, the term "$C_{2-12}$-alkenyl" covers linear, cyclic or branched hydrocarbon groups having 2 to 12 carbon atoms and comprising one unsaturated bond. Examples of alkenyl groups are vinyl, allyl, butenyl, pentenyl, hexenyl, heptenyl, octenyl, dodecaenyl. Analogously, the term "$C_{2-6}$-alkenyl" is intended to cover linear, cyclic or branched hydrocarbon groups having 2 to 6 carbon atoms and comprising one unsaturated bond. Preferred examples of alkenyl are vinyl, allyl, butenyl, especially allyl.

Similarly, the term "$C_{2-12}$-alkynyl" means a linear or branched hydrocarbon group having 2 to 12 carbon atoms and comprising a triple bond. Examples hereof are ethynyl, propynyl, butynyl, octynyl, and dodecanyl.

In the present context, i.e. in connection with the terms "alkyl", "alkenyl", and "alkynyl", the term "optionally substituted" means that the group in question may be substituted one or several times, preferably 1–3 times, with group(s) selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkoxycarbonyl, $C_{1-6}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, sulphono, $C_{1-6}$-alkylsulphonyloxy, nitro, sulphanyl, $C_{1-6}$-alkylthio, halogen, where any aryl and heteroaryl may be substituted as specifically describe below for "optionally substituted aryl and heteroaryl".

Preferably, the substituents are selected from hydroxy, $C_{1-6}$-alkoxy, carboxy, $C_{1-6}$-alkoxycarbonyl, $C_{1-6}$-alkylcarbonyl, formyl, aryl, aryloxycarbonyl, arylcarbonyl, heteroaryl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, carbamido, halogen, where aryl and heteroaryl may be substituted 1–5 times, preferably 1–3 times, with $C_{1-4}$-alkyl, $C_{1-4}$-alkoxy, nitro, cyano, amino or halogen. Especially preferred examples are hydroxy, $C_{1-6}$-alkoxy, carboxy, aryl, heteroaryl, amino, mono- and di($C_{1-6}$-alkyl)amino, and halogen, where aryl and heteroaryl may be substituted 1–3 times with $C_{1-4}$-alkyl, $C_{1-4}$-alkoxy, nitro, cyano, amino or halogen.

In the present context the term "aryl" means a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heteroaryl" means a fully or partially aromatic carbocyclic ring or ring system where one or more of the carbon atoms have been replaced with heteroatoms, e.g. nitrogen (=N— or —NH), sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrazinyl, pyridazinyl, piperidinyl, coumaryl, furyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl, phenoxazonyl.

In the present context, i.e. in connection with the terms "aryl" and "heteroaryl", the term "optionally substituted" means that the group in question may be substituted one or several times, preferably 1–5 times, in particular 1–3 times) with group(s) selected from hydroxy (which when present in an enol system may be represented in the tautomeric keto form), $C_{1-6}$-alkyl, $C_{1-6}$-alkoxy, oxo (which may be represented in the tautomeric enol form), carboxy, $C_{1-6}$-alkoxycarbonyl, $C_{1-6}$-alkylcarbonyl, formyl, aryl, aryloxy, aryloxy-carbonyl, arylcarbonyl, heteroaryl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, sulphono, $C_{1-6}$-alkylsulphonyloxy, nitro, sulphanyl, dihalogen-$C_{1-4}$-alkyl, trihalogen-$C_{1-4}$-alkyl, halogen, where aryl and heteroaryl representing substituents may be substituted 1–3 times with $C_{1-4}$-alkyl, $C_{1-4}$-alkoxy, nitro, cyano, amino or halogen. Preferred examples are hydroxy, $C_{1-6}$-alkyl, $C_{1-6}$-alkoxy, carboxy, $C_{1-6}$-alkoxycarbonyl, $C_{1-6}$-alkylcarbonyl, aryl, amino, mono- and di($C_{1-6}$-alkyl)amino, and halogen, wherein aryl may be substituted 1–3 times with $C_{1-4}$-alkyl, $C_{1-4}$-alkoxy, nitro, cyano, amino or halogen.

"Halogen" includes fluoro, chloro, bromo, and iodo.

It should be understood that oligomers (LNA modified oligonucleotides) and LNAs as such include possible salts thereof, of which pharmaceutically acceptable salts are especially relevant. Salts include acid addition salts and basic salts. Examples of acid addition salts are hydrochloride salts, sodium salts, calcium salts, potassium salts, etc. Examples of basic salts are salts where the (remaining) counter ion is selected from alkali metals, such as sodium and potassium, alkaline earth metals, such as calcium, and ammonium ions ($^+$N(R$^g$)$_3$R$^h$, where each of R$^g$ and R$^h$ independently designates optionally substituted $C_{1-6}$-alkyl, optionally substituted $C_{2-6}$-alkenyl, optionally substituted aryl, or optionally substituted heteroaryl). Pharmaceutically acceptable salts are, e.g., those described in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology. Thus, the term "an acid addition salt or a basic salt thereof" used herein is intended to comprise such salts. Furthermore, the oligomers and LNAs as well as any intermediates or starting materials therefor may also be present in hydrate form.

EXAMPLES

Although no specific working examples are included in the present application, it is believed that suitable examples could be those specifically described in WO 96/29431 where the advantages obtained of using LNA modified oligonucleotides can be further illustrated.

What is claimed is:

1. A process for detecting a target nucleic acid sequence or a mutation in a nucleic acid molecule, comprising:
   a) hybridising an LNA modified oligonucleotide to the nucleic acid molecule or an amplified product thereof;
   b) detecting a hybrid formed in step (a) by mass spectrometry
      wherein said detecting indicates the presence of said target nucleic acid sequence or said mutation.

2. The process according to claim 1, wherein the LNA modified oligonucleotide which is hybridised to the nucleic acid molecule is selected from the group consisting of detector oligonucleotides, capture oligonucleotides, primers, extended primers, ligation educts and ligation products.

3. The process according to claim 1, further comprising the step of determining the sequence of one or more nucleotides conprised within the target nucleic acid sequence or within the sequence comprising the mutation.

4. The process according to claim 1, wherein the target nucleic acid sequence is a DNA fingerprint or is implicated in a disease or condition selected from the group consisting of a genetic disease, a chromosomal abnormality, a genetic predisposition, a viral infection, a fungal infection, a bacterial infection and a protist infection.

5. The process according to claim 1, comprising the steps of:
   a) obtaining the nucleic acid molecule from a biological sample;
   b) immobolising the nucleic acid molecule onto a solid support, to produce an immobilised nucleic acid molecule;
   c) hybridising a detector oligonucleotide with the immobilised nucleic acid molecule and removing unhybridised detector oligonucleotide;
   d) ionising and violatilising the product of step c); and
   e) detecting the detector oligonucleotide indicates the presence of the detection of the detector oligonucleotide indicates the presence of the target nucleic acid sequence in the biological sample.

6. The process according to claim 5, wherein the detector oligonucleotide comprises an LNA modified nucleotide.

7. A process according to claim 1, wherein the detector oligonucleotide is an LNA modified oligonucleotide.

8. A process according to claim 1, wherein the amplification product is produced by a procedure selected from the group consiting of: cloning, transcription based amplification, the polymerase chain reacton (PCR), the ligase chain reaction, (LCR), and strand displacement amplification (SDA).

9. A process for detecting a target nucleic acid sequence present in a biological sample, comprising the steps of:
   a) obtaining a target nucleic acid sequence from a biological sample;
   b) replicating the target sequence, thereby producing a replicated nucleic acid molecule;
   c) specifically digesting the replicated nucleic acid molecule using at least one nuclease, thereby producing digested fragments;
   d) immobilizing the digested fragments onto a solid support containing complementary capture nucleic acid sequences to produce immobilized fragments;
   e) analyzing the immobolized fragments by mass spectrometry,
      wherein the presence of immobilized fragments and the determination of the molecular weights of the immobolized fragments provide information on the target nucleic acid sequence, and
      wherein either the digested fragments or the capture nucleic acids comprise at least one LNA molecule.

10. The process according to claim 9, wherein the complementary capture nucleic acid molecules are LNA modified oligonucleotides.

11. The method according to claim 10, wherein the number of LNA molecules varies among different capture molecules.

12. A process for detecting a target nucleic acid sequence present in a biological sample comprising the steps of:
   a) obtaining a nucleic acid molecule containing a target nucleic acid sequence for a biological sample;
   b) contacting the target nucleic acid sequence with at least one primer, said primer having 3' terminal base complementarity to the target nucleic acid sequence;
   c) contacting the product of step b) with an polymerase enzyme and sequentially with one of the four nucleoside triphosphates;
   d) ionizing and volatizing the product of step c); and
   e) detecting the product of step d) by mass spectrometry,
      wherein the molecular weight of the product indicates the presence or absence of a mutation next to the 3' end of the primer in the target nucleic acid sequence;
      and wherein at least one of the primer or extension products of step c) comprises at least one LNA molecule.

13. A process according to claim 12, wherein the primer is an LNA modified oligonucleotide.

14. A process for detecting a target nucleotide present in a biological sample, comprising the steps of:
   a) obtaining a nucleic acid molecule that contains a target nucleotide;
   b) immobilising the nucleic acid molecule onto a solid support to produce an immobilised nucleic acid molecule;
   c) hybridizing the immobilized nucleic acid molecule onto a solid support, with a primer oligonucleotide that is complementary to the nucleic acid molecule at a site immediately 5' of the target nucleotide;
   d) contacting the product of step c) with a complete set of dideozynucleosides or 3' deoxynucleoside triphosphates and a DNA dependent DNA polymerase, so that only the deoxynucleoside or nucleoside triphosphate that is complementary to the target nucleotide is extended onto the primer;
   e) ionizing and volatilising the product of step d); and detecting the extended primer by mass spectrometry, to determine the identity of the target nucleotide;

wherein at least one of the primer or the extended primer comprises at least one LNA molecule.

15. The process according to claim 14, wherein the extended primer is an LNA modified oligonucleotide.

16. A process for detecting a mutation in a nucleic acid molecule, comprising the steps of:
   a) obtaining a nucleic acid molecule;
   b) hybridizing the nucleic acid molecule with an oligonucleotide probe, thereby forming a mismatch at the site of mutation;
   c) contacting the product of step b) with a single strand specific endonuclease;
   d) ionizing and volatilising the product of step c); and
   e) detecting the products obtained by mass spectrometry, wherein the presence of more than one fragment, indicates that the nucleic acid molecule contins a mutation, and wherein the probe comprises at least one LNA molecule.

17. A process for detecting a target nucleic acid sequence present in a biological sample, comprising the steps of:
   a) obtaining a nucleic acid containing a target nucleic acid sequence from a biological sample;
   b) performing at least one hybridization of the target nucleic acid sequence with a set of ligation educts and a thermostable DNA ligase, thereby forming a ligation product;
   c) ionizing and volatilising the product of step b); and
   d) detecting the ligation product by mass spectrometry thereby detecting the presence of the target nucleic acid sequence wherein at least one of the ligation educts is an LNA modified oligonucleotide.

* * * * *